US010908165B2

(12) United States Patent
Ayrton et al.

(10) Patent No.: US 10,908,165 B2
(45) Date of Patent: Feb. 2, 2021

(54) METHOD FOR DETERMINING WHETHER A PEPTIDE COMPRISES ASPARTATE OR ISOASPARTATE

(71) Applicants: Purdue Research Foundation, West Lafayette, IN (US); AMGEN INC., Thousand Oaks, CA (US)

(72) Inventors: Stephen T. Ayrton, West Lafayette, IN (US); Robert Graham Cooks, West Lafayette, IN (US); Tawnya Flick, Thousand Oaks, CA (US); Da Ren, Thousand Oaks, CA (US)

(73) Assignees: Purdue Research Foundation, West Lafayette, IN (US); AMGEN INC., Thousand Oaks, CA (US)

( * ) Notice: Subject to any disclaimer, the term of this patent is extended or adjusted under 35 U.S.C. 154(b) by 182 days.

(21) Appl. No.: 16/002,749

(22) Filed: Jun. 7, 2018

(65) Prior Publication Data

US 2018/0356426 A1 Dec. 13, 2018

Related U.S. Application Data

(60) Provisional application No. 62/516,143, filed on Jun. 7, 2017.

(51) Int. Cl.
*G01N 33/68* (2006.01)
*H01J 49/10* (2006.01)
*H01J 49/00* (2006.01)

(52) U.S. Cl.
CPC ...... *G01N 33/6848* (2013.01); *H01J 49/0031* (2013.01); *H01J 49/10* (2013.01)

(58) Field of Classification Search
None
See application file for complete search history.

(56) References Cited

PUBLICATIONS

Castet et al. (1996) "Characterization of Aspartic Acid and Beta-Aspartic Acid in Peptides by Fast-atom Bombardment Mass Spectrometry and Tandem Mass Spectrometry," Rapid Communications in Mass Spectrometry, 10:1934-1938.
Cournoyer et al. (2005) "Deamidation: Differentiation of aspartyl from isoaspartyl products in peptides by electron capture dissociation," Protein Science, 14:452-463.
Gonzalez et al. (2000) "Differentiating alpha- and beta-aspartic acids by electrospray ionization and low-energy tandem mass spectrometry," Rapid Communications in Mass Spectrometry, 14:2092-2102.

(Continued)

*Primary Examiner* — Xiaoyun R Xu
(74) *Attorney, Agent, or Firm* — Lathrop GPM LLP; Brian C. Trinque, Esq.

(57) ABSTRACT

The invention generally relates to methods for determining whether a peptide includes aspartate or isoaspartate. In certain aspects, methods of the invention involve binding an aspartate/isoaspartate residue in a peptide with a label to produce a labeled peptide. The labeled peptide is then ionized. The ionizing process causes the label to undergo rearrangement in a gas phase at a higher rate if the label is bound to the aspartate residue as compared to if the label is bound to the isoaspartate residue. The methods of the invention then involve performing a mass spectrometry analysis to detect the rearrangement of the label, thereby determining whether the peptide includes aspartate or isoaspartate.

18 Claims, 21 Drawing Sheets

(56) References Cited

PUBLICATIONS

Liu et al. (2012) "Protein Isoaspartate Methyltransferase-Mediated 18O-Labeling of Isoaspartic Acid for Mass Spectrometry Analysis," Anal. Chem., 84:1056-1062.

Ni et al. (2010) "Analysis of Isoaspartic Acid by Selective Proteolysis with Asp-N and Electron Transfer Dissociation Mass Spectometry," Anal. Chem., 82:7485-7491.

O'Connor et al. (2006) "Differentiation of Aspartic and Isoaspartic Acids Using Electron Transfer Dissociation," J. Am. Soc. Mass Spectrom, 17:15-19.

Puri et al. (2017) "A Flourescence-Based High-Throughput Coupled Enzymatic Assay for Quantitation of Isoaspartate in Proteins and Peptides," AAPS PharmaSciTech, 18(3):803-808.

Winter et al. (2009) "Separation of peptide isomers and conformers by ultra performance liquid chromatography," J. Sep. Sci., 32:1111-1119.

Yu et al. (2015) "In-Source decay characterization of isoaspartate and Beta-peptides," International Journal of Mass Spectrometry, 390:101-109.

Zheng et al. (2017) "Distinguishing D- and L-aspartic and isoaspartic acids in amyloid Beta peptides with ultrahigh resolution ion mobility spectrometry," Chem. Commun., 53:7913-7916.

Shimizu et al. (2005) "Biological Significance of Isoaspartate and Its Repair System," Biol. Pharm. Bull., 28(9):1590-1596.

Carpino et al. (1999) "The Diisopropylcarbodiimide/1-Hydroxy-7-azabenzotriazole System: Segment Coupling and Stepwise Peptide Assembly," Tetrahedron, 55:6813-6830.

Schotman et al. (1991) "Mechanism of the reaction of carbodiimides with carboxylic acids," Recl. Trav. Chim. Pays-Bas, 110:319-324.

Iwasawa et al. (2007) "Reaction of an introverted carboxylic acid with carbodiimide," Tetrahedron, 63:6506-6511.

Gilles et al. (1990) "Stability of Water-Soluble Carbodiimides in Aqueous Solution," Analytical Biochemistry, 184:244-248.

Bowen et al. (1991) "Ion-Neutral Complexes," Acc. Chem. Res., 24:364-371.

Kozin et al. (2016) "Amyloid-Beta containing isoaspartate 7 as potential biomarker and drug target in Alzheimer's disease," Focus Article, Mendeleev Commun., 26:269-275.

DeGruyter et al. "Residue-Specific Peptide Modification: A Chemist's Guide" Biochemistry Aug. 1, 2017; 56(30): 3863-3873.

DeGruyter et al. "Residue-Specific Peptide Modification: A Chemist's Guide" Supporting Information Biochemistry. Aug. 1, 2017; 56(30): 3863-3873.

Ayman El-Faham, Fernando Albericio, "Peptide Coupling Reagents, More than a Letter Soup" Chem. Rev., Aug. 26, 2011, 111:6557-6602.

Alexander Leitner and Wolfgang Lindner, Chemistry Meets Proteomics: The use of chemical tagging reactions for MS-based proteomics, proteomics-journal.com Jun. 19, 2006, 5418-5434.

METHOD FOR DETERMINING WHETHER A PEPTIDE COMPRISES ASPARTATE OR ISOASPARTATE

CROSS-REFERENCE TO RELATED APPLICATIONS

This application claims the benefit of U.S. Provisional Application No. 62/516,143, filed Jun. 7, 2017, the contents of which are incorporated herein by reference in its entirety.

FIELD OF THE INVENTION

The invention generally relates to methods for determining whether a peptide includes aspartate or isoaspartate.

BACKGROUND

In vitro and in vivo isomerization of aspartate (Asp) to isoaspartate (isoAsp) is one of the main routes to protein degradation. Deamidation of asparagine (Asn) can also yield isoAsp via a common succinimide intermediate. Not only can this transformation change the structure and activity of a protein, it can also lead to immunological response. Furthermore, an increase in endogenous isoAsp has been linked to Alzheimer's disease and aging. The body naturally produces enzymes that work to reduce the levels of isoAsp, namely protein-L-isoaspartate (D-aspartate) O-methyltransferase (PIMT, PCMT), both of which methylate isoAsp to encourage isomerization to Asp.

The spontaneous, post-translational generation of isoAsp poses an immediate problem to the development of protein-bound pharmaceuticals, where shelf-life and activity may be directly affected; in fact, isoAsp generation is one of the most common contributors to heterogeneity in a protein-bound drug. Factors involved in the generation of isoAsp include pH, secondary and tertiary protein structure, and formulation.

Methods for the detection of isoAsp vary in complexity. An enzymatic, fluorescence based assay has recently been reported, which has a significant time requirement. High-performance liquid chromatography (HPLC) has been used to separate Asp/isoAsp containing peptides. The success of this method largely relies on changes in the secondary structures of medium-large peptides induced by isomerization. Mass spectrometric methods are probably the most widely reported, specifically electron transfer dissociation (ETD), electron capture dissociation (ECD) or $^{18}O$ labelling. ETD and ECD yield specific fragment ions for isoAsp, facilitating detection. Methods of $^{18}O$ labelling initially involve the selective enzymatic conversion of isoAsp to the succinimide intermediate, followed by hydrolysis with heavy water.

Recently, matrix-assisted laser desorption/ionization mass spectrometry (MALDI-MS) has been utilized to differentiate beta peptides (peptides containing an amino acid wherein the amino group is bound to the beta carbon instead of the alpha carbon as found naturally). Issues with MALDI include poor detection at the low mass range and poor performance with regard to quantitation.

SUMMARY

The invention provides methods to determine aspartate/isoaspartate by chemical derivatization. A peptide labeling reagent (e.g., 1-Ethyl-3-(3-dimethylaminopropyl)carbodiimide (EDC)) is used to label an aspartate/isoaspartate residue within a peptide backbone. The labeled peptide is then ionized, whereupon it undergoes rearrangement in the gas-phase. The rearrangement occurs at a higher rate for aspartate relative to isoaspartate, facilitating determination of whether the peptide includes aspartate or isoaspartate, which determination can optionally be quantitative.

In another aspect, disclosed herein is a method for determining whether a peptide comprises aspartate or isoaspartate, the method comprising binding an aspartate/isoaspartate residue in a peptide with a label to produce a labeled peptide; ionizing the labeled peptide, wherein the ionizing causes the label to undergo rearrangement in a gas phase at a higher rate if the label is bound to an aspartate residue as compared to if the label is bound to an isoaspartate residue; and performing a mass spectrometry analysis to detect the rearrangement of the label, thereby determining whether the peptide comprises aspartate or isoaspartate. In an embodiment, the relative abundance of certain byproducts is higher than the abundance of another byproduct if the peptide comprises isoaspartate.

In another aspect, disclosed herein is a method for determining whether an aspartate residue in a peptide has isomerized to isoaspartate, the method comprising binding an aspartate/isoaspartate residue in a peptide with a label to produce a labeled peptide; ionizing the labeled peptide, wherein the ionizing causes the label to undergo rearrangement in a gas phase at a higher rate if the label is bound to an aspartate residue as compared to if the label is bound to an isoaspartate residue; and performing a mass spectrometry analysis to detect the rearrangement of the label, thereby determining whether the peptide comprises aspartate or isoaspartate. In an embodiment, the rate of rearrangement is ascertained by determining the abundance of a labeled peptide fragment having a specific mass compared to the abundance of a labeled peptide fragment having a different mass.

In an embodiment, the rate of rearrangement of the label is determined by measuring the ratio of peptide fragments in a mass spectrum. In embodiments of the methods, the ionization can take place separately from mass spectrometry or simultaneously with mass spectrometry. In particular embodiments, the invention utilizes a typical carboxylic acid coupling reagent, 1-ethyl-3-(3-dimetylaminopropyl)carbodiimide (EDC). This reagent exhibits by-product formation by rearrangement at a relatively high rate. The major by-product of EDC-bound peptides (which are acylisoureas, AiUs) is N-acylurea (NAU) formed by N—O migration at the carboxylate to which EDC is bound. The invention takes advantage of the by-product formation by EDC and uses, in certain embodiments, mass spectrometry to isolate and analyze the isobaric ions corresponding to NAU and AiU. Specifically, the loss of neutral isocyanate from NAU may be measured against fragments of AiU ions in the product ion CID (collision-induced dissociation) mass spectra of various peptides. This ratio may then be used to interpret the percentage of isoAsp present in a given sample.

In certain aspects, methods of the invention involve binding an aspartate/isoaspartate residue in a peptide with a label to produce a labeled peptide. The labeled peptide is then ionized. The ionizing process causes the label to undergo rearrangement in a gas phase at a higher rate if the label is bound to the aspartate residue as compared to if the label is bound to the isoaspartate residue. The methods of the invention then involve performing a mass spectrometry analysis to detect the rearrangement of the label, thereby determining whether the peptide includes aspartate or isoaspartate.

Other aspects of the invention provide methods for determining whether a peptide includes aspartate or isoaspartate that involve detecting a gas phase rearrangement of a label bound to an aspartate/isoaspartate residue of a peptide, wherein the label rearranges at a higher rate in the gas phase if the label is bound to the aspartate residue as compared to if the label is bound to the isoaspartate residue.

In another aspect, disclosed herein is a method for determining whether a peptide comprises aspartate or isoaspartate, the method comprising detecting a gas phase rearrangement of a label bound to an aspartate/isoaspartate residue of a peptide by determining the abundance of a labeled peptide fragment having a specific mass compared to the abundance of a labeled peptide fragment having a different mass, wherein the label rearranges at a higher rate in the gas phase if the label is bound to the aspartate residue as compared to if the label is bound to the isoaspartate residue.

In yet another aspect, disclosed herein is a method for determining whether a peptide comprises aspartate that has isomerized to isoaspartate, the method comprising detecting a gas phase rearrangement of a label bound to an aspartate/isoaspartate residue of a peptide by determining the abundance of a labeled peptide fragment having a specific mass compared to the abundance of a labeled peptide fragment having a different mass, wherein the label rearranges at a higher rate in the gas phase if the label is bound to the aspartate residue as compared to if the label is bound to the isoaspartate residue.

As mentioned above, a preferable labeling reagent is 1-ethyl-3-(3-dimethylaminopropyl)carbodiimide (EDC). However, the skilled artisan will appreciate that other labeling reagents are within the scope of the invention. The labeling agents used in the methods disclosed herein include but are not limited to other carbodiimides. Like EDC, other labeling reagents would be able to undergo a rearrangement in the gas phase at a higher rate for one residue over the other. That is, any other labeling reagents would be able to undergo a rearrangement in the gas phase at a higher rate if the label is bound to the aspartate residue as compared to if the label is bound to the isoaspartate residue. Alternatively, any other labeling reagents would be able to undergo a rearrangement in the gas phase at a higher rate if the label is bound to the isoaspartate residue as compared to if the label is bound to the aspartate residue. For example, dicyclohexyl carbodiimide (DCC) could also be used as a labeling reagent. Without being limited by any particular theory or mechanism of action, it is believed that the carbodiimide is the group in the above molecules that causes the label to undergo rearrangement in a gas phase. Accordingly, the skilled artisan will appreciate that any labeling reagent that includes a carbodiimide group can be used with methods of the invention.

In certain exemplary embodiments, the EDC binds a carboxylate group of the aspartate/isoaspartate residue. In such embodiments, the rearrangement includes production of N-acylurea (NAU). The mass spectrometry analysis to detect the rearrangement of the label may include collision-induced dissociation of the NAU to detect ethyl isocyanate ions. The mass spectrometry analysis may also detect the labeled peptide as acylisourea (AiU). The mass spectrometry analysis to detect the AiU may include collision induced dissociation of the AiU to detect fragment ions of the AiU. The methods of the invention may further include quantifying an amount of isoaspartate in the peptide by determining a ratio of the ethyl isocyanate ions to the fragment ions of the AiU.

The methods of the invention may also involve providing a sample (such as a mammalian (e.g., human) tissue or body fluid sample) including a protein that includes an aspartate/isoaspartate residue. The methods may then involve digesting the protein to produce a peptide that comprises the aspartate/isoaspartate residue.

BRIEF DESCRIPTION OF THE DRAWINGS

FIG. 11A shows the effect of ion activation energy on the ratios of the fragments of AiU/NAU in the CID product ion mass spectra of ALD(iso)GK peptide. FIG. 11B shows the effect of the voltage applied to the tube lens on the ratios of the fragments of AiU/NAU in the CID product ion mass spectra of ALD(iso)GK peptide. FIG. 11C shows the effect of in-source ion activation energy on the ratios of the fragments of iAU/NAU in the CID product ion mass spectra of ALD(iso)GK peptide.

DETAILED DESCRIPTION

Figure 1A:
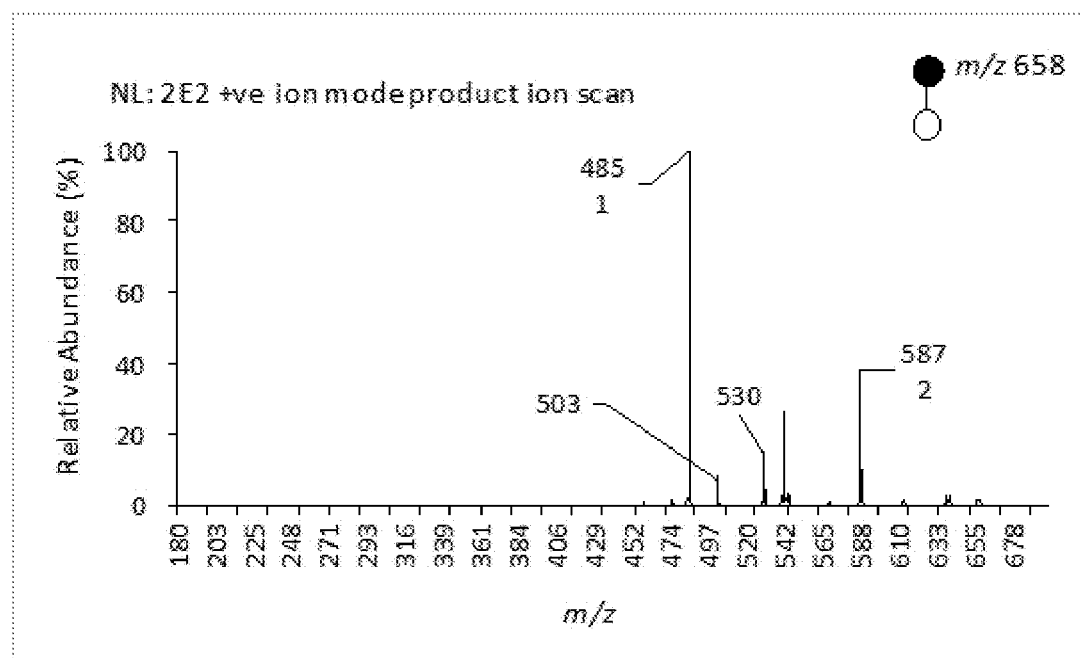
FIG. 1A and FIG. 1B show the positive ion mode CID product ion mass spectrum of EDC-bound ALDisoGK peptide (FIG. 1A) and EDC-bound ALDGK peptide (FIG. 1B).

The invention takes advantage of the recognition that peptides bearing an Asp residue have a very specific arrangement of functional groups relative to those bearing isoAsp. IsoAsp is a β-peptide while Asp is naturally an α-peptide. This has the potential to change the chemistry of the residue, particularly with regards to the steric aspects of the system.

The data herein and in the Examples below illustrate that the methods of the invention provide a new, fast, and inexpensive manner to determine the presence of isoAsp in a peptide. The methods of the invention work with peptides of different lengths, including one model peptide from an anti-streptavidin digest. The chemistry behind the success of the method has been explored, and this constitutes the simplest and most accessible assay for isoAsp determination, which makes it fundamentally useful to those wishing to study its link to disease or drug-bioconjugate degradation.

Definitions

The term "peptide," as used herein, refers to a chain of two or more amino acids that are linked together with peptide or amide bonds, regardless of post-translational modification (e.g., glycosylation or phosphorylation). In preferred embodiments, the peptide contains at least one aspartate or at least one isoaspartate residue. In some embodiments of the methods disclosed herein, the peptides are between 2-100 amino acids. In some embodiments of the methods disclosed herein, the peptides are between 2-7 amino acids. In some embodiments of the methods disclosed herein, the peptides are more than 7 amino acids or no more than 100 amino acids. In some embodiments, the peptides of the methods disclosed herein are fragments of a protein following digestion with a protease.

The terms "binding," "reacting," and "contacting," as used herein, are used interchangeably and refer to an interaction between a label and a peptide.

The term "label," as used herein, refers to a detectable compound or composition that is conjugated directly or indirectly to the peptide. The label may itself be detectable (e.g., radioisotope labels or fluorescent labels) or, in the case of an enzymatic label, may catalyze chemical alteration of a substrate compound or composition which is detectable. In some embodiments, the label is a carbodiimide. In some embodiments, the carbodiimide label is selected from the group consisting of dicyclohexylcarbodiimide (DCC), diisopropylcarbodiimide (DIC), and 1-Ethyl-3-(3'-dimethylaminopropyl)carbodiimide (EDC). In an embodiment, the carbodiimide label is dicyclohexylcarbodiimide (DCC). In an embodiment, the carbodiimide label is diisopropylcarbodiimide (DIC). In an embodiment, the carbodiimide label is 1-Ethyl-3-(3'-dimethylaminopropyl)carbodiimide (EDC).

The term "labeled peptide fragment" as used herein, refers to a byproduct of the labeled peptide following ionization. In some embodiments, the labeled peptide fragment is N-acylurea (NAU) or an ion fragment thereof. In other embodiments, the labeled peptide fragment is acylisourea (AiU) or an ion fragment thereof.

The term "ionize" or "ionization" as used herein, refer to the production of gas phase ions suitable for detection in mass spectrometry from the labeled peptide. The ionization can take place separately from mass spectrometry or simultaneously with mass spectrometry.

The term "production" or "creation" as used herein, refer to the formation of a certain byproduct of a labeled peptide following ionization.

The term "digest" as used herein, refers to an enzymatic degradation of proteins or peptides into smaller peptides using a protease. In some embodiments, the protease is trypsin or pepsin.

Methods

The invention provides methods to determine aspartate/isoaspartate by chemical derivatization. A peptide labeling reagent (e.g., 1-Ethyl-3-(3-dimethylaminopropyl)carbodiimide (EDC)) is used to label an aspartate/isoaspartate residue within a peptide backbone. The labeled peptide is then ionized, whereupon it undergoes rearrangement in the gas-phase. The rearrangement occurs at a higher rate for aspartate relative to isoaspartate, facilitating determination of whether the peptide includes aspartate or isoaspartate, which determination can optionally be quantitative.

Figure 1B:
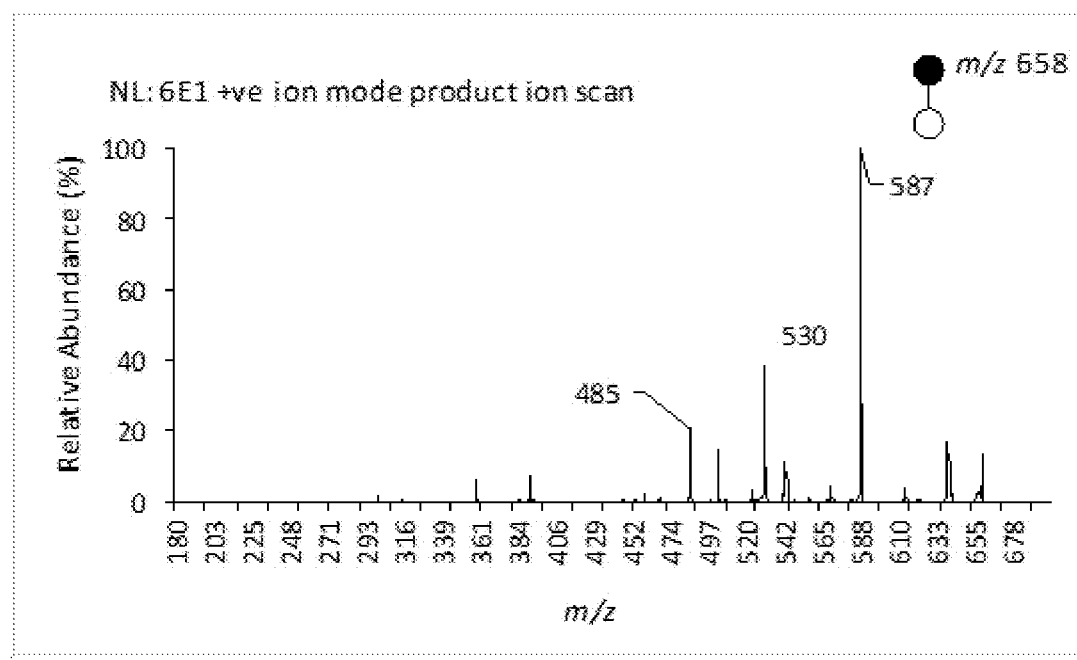

FIGS. 1A-B show the CID product ion mass spectra of Ala-Leu-Asp-Gly-Lys (ALDGK) peptide and Ala-Leu-isoAsp-Gly-Lys (ALDisoGK) peptide. This pentapeptide is a model for a peptide produced from a digest of anti-streptavidin. The spectra are distinctly different; one is dominated by the loss of the urea derived from EDC (EDU) (m/z 485) and the other is dominated by the loss of ethyl isocyanate (m/z 587). A less-dominant primary fragment ion signal corresponds to the loss of 3-dimethylaminopropylisocyanate (m/z 530).

Isocyanates are known degradation products of N-acyl urea (NAU), which is itself a by-product of rearrangement of EDC-bound carboxylate, acylisourea (AiU). The loss of isocyanate, therefore, is assigned to be a fragmentation of NAU; i.e. isocyanates cannot fragment away from the AiU ion. Conversely, the loss of urea is likely only to come from AiU ions; to fragment neutral urea from NAU would require the cleavage of what is essentially an amide/carbamate bond. Based on this interpretation, it can be seen that the AiU derived from a peptide bearing Asp can rearrange to its NAU by-product far more readily than its isoAsp bearing isomer.

Figure 16:
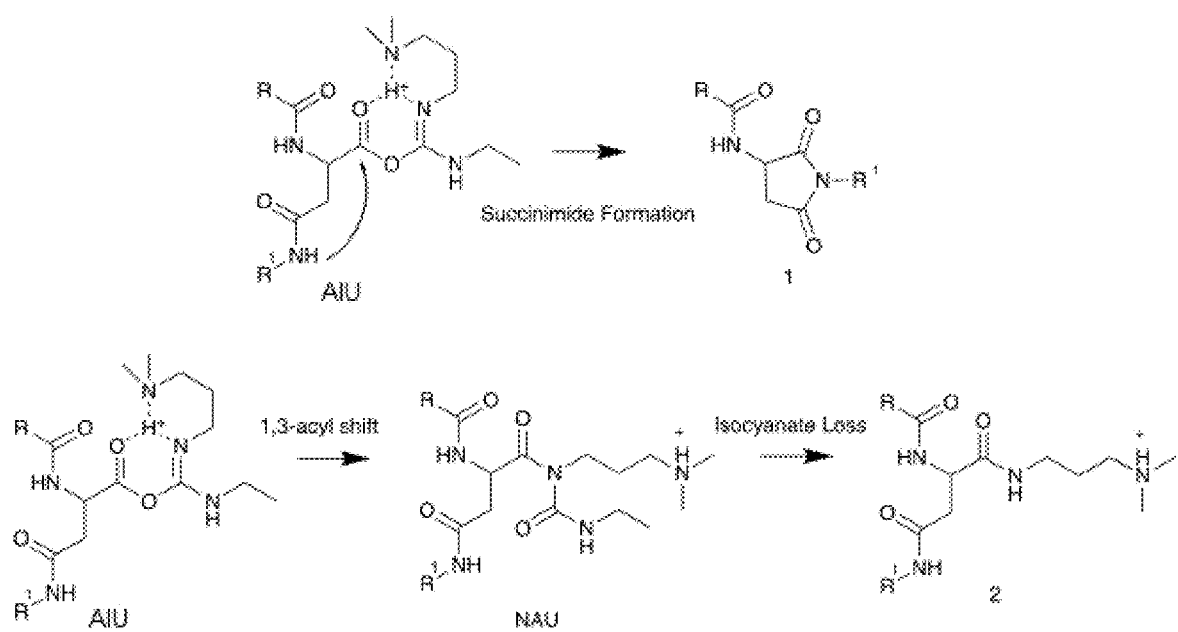
FIG. 16 shows a scheme for the production of succinimide and urea from protonated AiU ions and the loss of isocyanate from NAU ions

The loss of EDU can be explained in terms of the formation of a bond between the carboxylate to which EDC is bound and another atom, in this case the atom is a proximal nitrogen which attacks to form a succinimide ring structure (FIG. 16). Subsequent fragmentation provides evidence that the ions that yield the signal at m/z 485 are a combination of peptides bound to carbodiimides at the C terminus and peptides bound at the aspartate residue. The data is interpreted as a convolution of the fragmentation of these ion populations, with the fragmentation from the aspartate/isoaspartate-bound carbodiimide yielding spectral differences. This trend can be observed for the tripeptides DL/DisoL and LDA/LDisoA and the hexapeptides GDLLLK/GDisoLLLK. (See Examples). The below discusses the fact that the rearrangement is a controllable gas phase rearrangement.

Figure 2A:
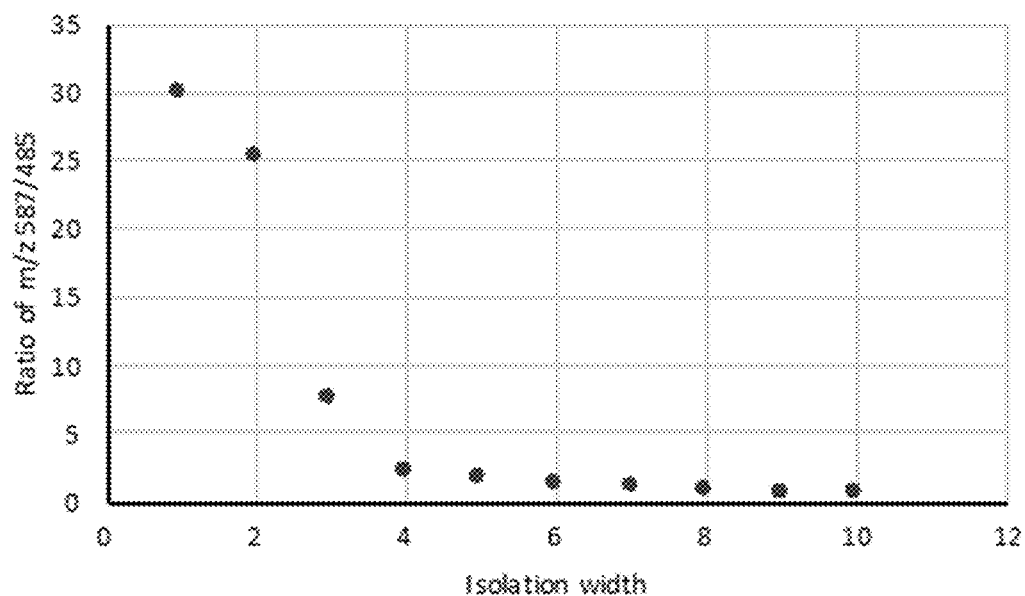
FIG. 2A and FIG. 2B show the effect of isolation width on the ratio of m/z 587/485 in the CID product ion mass spectrum of EDC-bound ALDisoGK peptide (FIG. 2A) and ALDGK peptide (FIG. 2B).
Figure 2B:
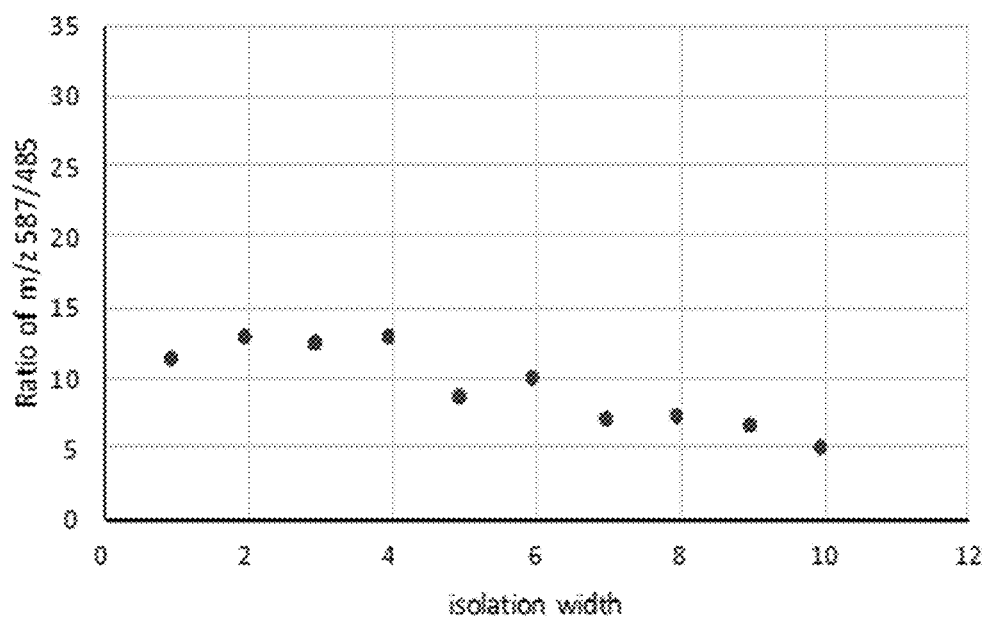

FIGS. 2A-B show the effect of the isolation width used in the CID experiment plotted against the ratio of ions in the product ion spectrum of EDC-bound ALDisoGK. Clearly, there was a remarkable effect. When an ion was isolated in an ion trap, an isolation waveform was applied. In principle, the isolation waveform should have consisted of all of the frequencies of other species within the ion trap other than the frequency that corresponded to the ion population of interest. The isolation waveform was applied at sufficient amplitude so as to destabilize the other ions. In practice, the ion population that is being isolated can be heated by the isolation waveform, as ions in an ion trap do not have discrete frequencies, but frequency distributions. This explains the observation of the apparent effect of the isolation width on the rearrangement reaction occurring in the gas phase.

In order to investigate whether ion activation before CID was in operation in this method, different methods of ion activation before CID were utilized and the effects recorded (Examples herein). When the offset between the tube lens and the skimmer cone/ion transfer capillary was maximized, the CID product ion mass spectrum was pushed towards those fragments which represent NAU. When in-source fragmentation was utilized, the ratio of species in the product ion mass spectrum could similarly be pushed towards those representing NAU. Both of these processes constitute an addition of energy to the ions before they reach the ion trap (i.e. before the CID event), but while energy is added, it is not as much as is added during CID; these parameters are usually used to dissociate loosely bound clusters rather than covalent bonds.

Another way to affect the ions in the CID product ion mass spectrum is to change the amount of time allowed for the ions to enter the trap, thereby changing how long they have to rearrange before the CID event. Surprisingly, this effect was very strong, indicating that the rearrangement of ions to NAU occurs on a timescale on the order of at least a portion of the MS experiment; milliseconds.

All of the above phenomena illustrate that the rearrangement of the ions to NAU is largely occurring in the gas phase. Mechanistically, there seems to be little to discriminate aspartate from isoaspartate, and the mechanism of rearrangement from AiU to NAU is considered to be an example of a 1,3-acyl shift. Bimolecular reaction has been ruled out due to the fact that it was highly unlikely that there would be effective collisions to generate such reactions between positively charged species in the ion trap.

Figure 17:
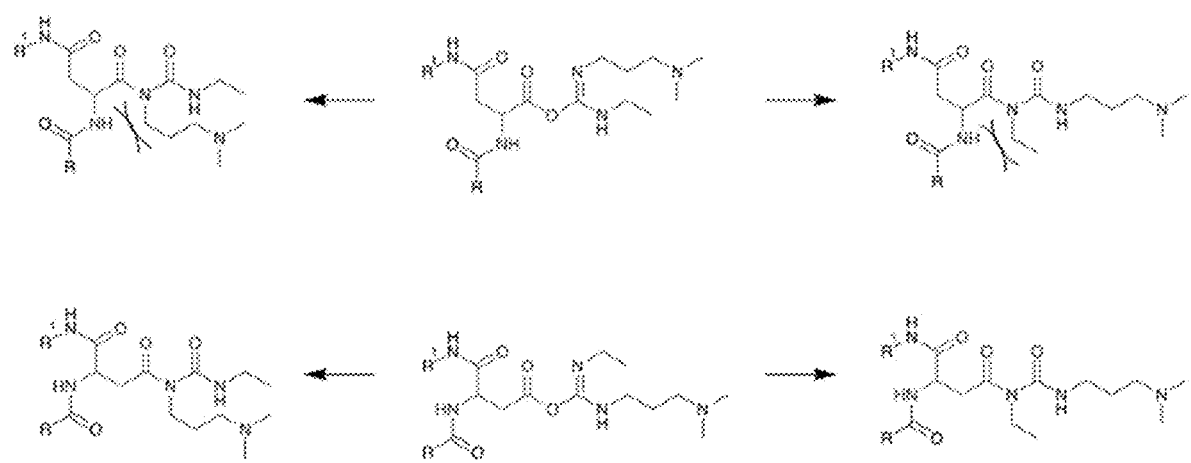
FIG. 17 shows a scheme for steric hindrance to rearrangement in isoAsp (top) and lack thereof in Asp (bottom)

Without being limited by any particular theory or mechanism of action, it is believed that this differential rate in the rearrangement of AiUs derived from Asp/isoAsp is sterics. FIG. 17 illustrates this process. Simply put, there should be a higher steric barrier to the formation of NAU in the case of isoAsp.

Again, without being limited by any particular theory or mechanism of action, it is believed that the difference in the rate of rearrangement to NAU between carbodiimide-bound Asp/isoAsp is the result of a higher energy barrier in isoAsp.

Using the peptide system ALDGK, which by virtue of the aspartate residue should favor rearrangement, and using instrumental conditions which left the least opportunity for rearrangement), the mass spectra of both EDC and DCC-bound ions were recorded. EDC-bound ions produced signals corresponding to the fragmentation of the AiU and NAU form of roughly equal intensity in their mass spectra. When DCC, a more sterically demanding carbodiimide, was used, the signal corresponding to the fragmentation of AiU was dominant in the mass spectrum. These results suggest that the more sterically demanding carbodiimide rearranged to the NAU less favorably (data in Examples herein). It should be noted that there was still a significant difference between the mass spectra of the DCC adducts of ALDGK and ALDisoGK, when the conditions were not chosen to push the system to the extreme of rearrangement to NAU or preservation of AiU.

When dealing with positively charged ions, species are typically protonated. One way to deal with positive ions without a proton is to use quaternary ammonium species. In this case, the methiodide form of EDC (MIEDC) was tested and its behavior recorded. In this case, the discrimination between the two peptides was severely diminished if not eliminated. There are a few possible explanations for this. The increased steric demand diminished the rearrangement to NAU in both cases or a proton is important mechanistically.

Figure 3:
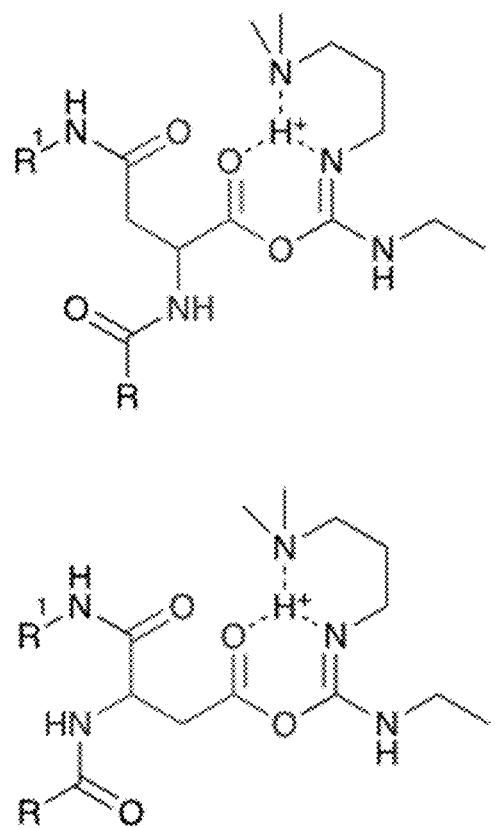
FIG. 3 shows protonated ions considered to be of importance to the observed chemistry.

The interpretation of the results is the latter, and it is asserted that this experiment reveals the importance of a proton. The experiments with DCC show that the nature of the substitution of the carbodiimide does not completely hinder the discrimination of the method. The proposed structure of the important ion is shown in FIG. 3. Of course, this is just one possible configuration of the protonated species, and the proton could be borne by the other nitrogen in the carbodiimide structure while retaining its association to the carboxylate carbonyl. That configuration might be favorable considering the steric penalty involved in bringing the dimethylamine close to the rest of the molecule.

The proton in question is likely to be associated with the diamine in the EDC species, but a conformation can be adopted to associate that proton with the carbonyl of the bound carboxylate. If that carbonyl does indeed have a proton associated with it, in principle it would serve to enhance its lability towards nucleophilic attack; it would promote the formation of the succinimide which is the fragment ion associated with AiU. This activation presumably brings the relatively unfavorable succinimide formation into a kinetic regime where it effectively competes with rearrangement to NAU.

The observed processes, then, can be summarized as follows. AiU ions can rearrange to NAU ions quite favorably, with small differences in rate due to steric effects. Protonated AiU ions can also expel urea molecules by ring-closure to form a succinimide at a comparable rate to NAU formation, and the rate of both of these processes is on the order of the mass spectrometry experiment; milliseconds.

Figure 4:
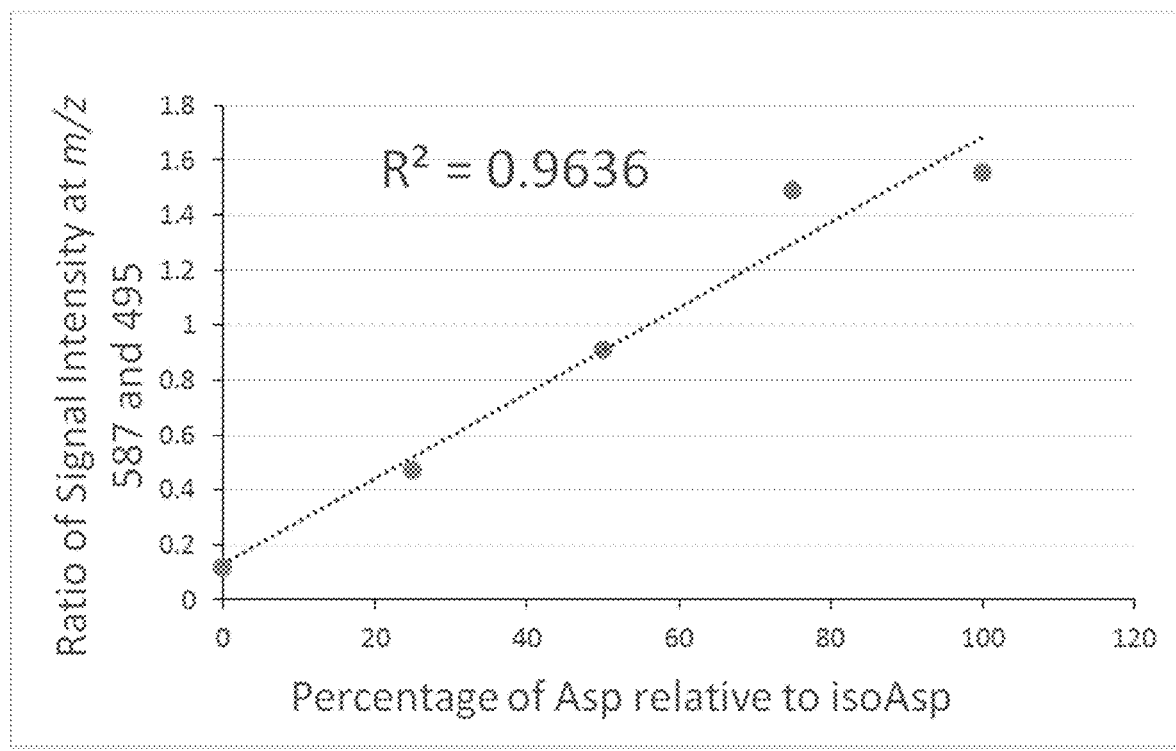
FIG. 4 is a chart showing calibration of ALD(iso)GK peptide.

FIG. 4 shows that the methods of the invention can be used for calibration. Particularly, FIG. 4 shows a calibration plot for the ALD(iso)GK system. Calibration curves for GD(iso)LLLK and LD(iso)A are given in the Examples. The percentage of isoaspartate to aspartate was calibrated in these plots.

Table 1 shows the ratios of discriminating ions in the CID product ion mass spectra of peptides bound to different diimides (small peptides have different discriminating fragmentation pathways).

TABLE 1

The ratio of fragment ions of the format AiU fragment:NAU fragment

| Peptide | EDC | DCC | DIC | MEIDC |
|---|---|---|---|---|
| DL | 0:1 | | | |
| DisoL | 1:0 | | | |
| LDA | 1:1000 | | | |
| LDisoA | 1:5.88 | | | |
| ALDGK | 1:5 | 1:0.22 | 1:3.7 | 1:0.15 |
| ALDisoGK | 1:0.5 | 1:0.03 | 1:0.43 | 1:0.35 |
| GDLLLK | 1:1.1 | | 1:0.13 | |
| GDisoLLLK | 1:0.2 | | 1:2.1 | |

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

EXAMPLES

Example 1: Materials and Methods

EDC, MIEDC, DCC were acquired from Sigma Aldrich (St. Louis, Mo.). Ethanol was acquired from Makron Fine Chemicals LTD (Avantor; Center Valley, Pa.). The peptide samples were purchased from Anaspec Inc. (Fremont, Calif.). Nanoelectrospray emitters were prepared using a micropipette tip puller (Sutter Instruments; Novato, Calif.). Analysis was conducted on a standard linear ion trap (LTQ, Thermo Scientific; San Jose, Calif.) or an Orbitrap (LTQ-Orbitrap XL, Thermo Scientific; San Jose, Calif.) instrument.

General method for sample preparation and analysis: A stock solution of carbodiimide was prepared (10 mM in 1:1 EtoH:$H_2O$). A sample of the peptide was prepared (1 mM in 1:1 EtoH:$H_2O$). Standard solutions for analysis by nanoelectrospray were prepared which contained both the peptide (500 µM, 1 eq.) and the carbodiimide (1 mM, 2 eq.). Analysis was conducted by loading a 10 µL ample into a nanoelectrospray emitter and then applying a potential of 1.5 kV.

The instrumental parameters for standard CID analysis were as follows: Capillary Voltage; 15 V, Tube Lens; 65 V, Capillary temperature; 150° C., Maximum ion injection time; 10 ms, isolation width; 5 units, collision energy; 25 arb.

Figure 5:
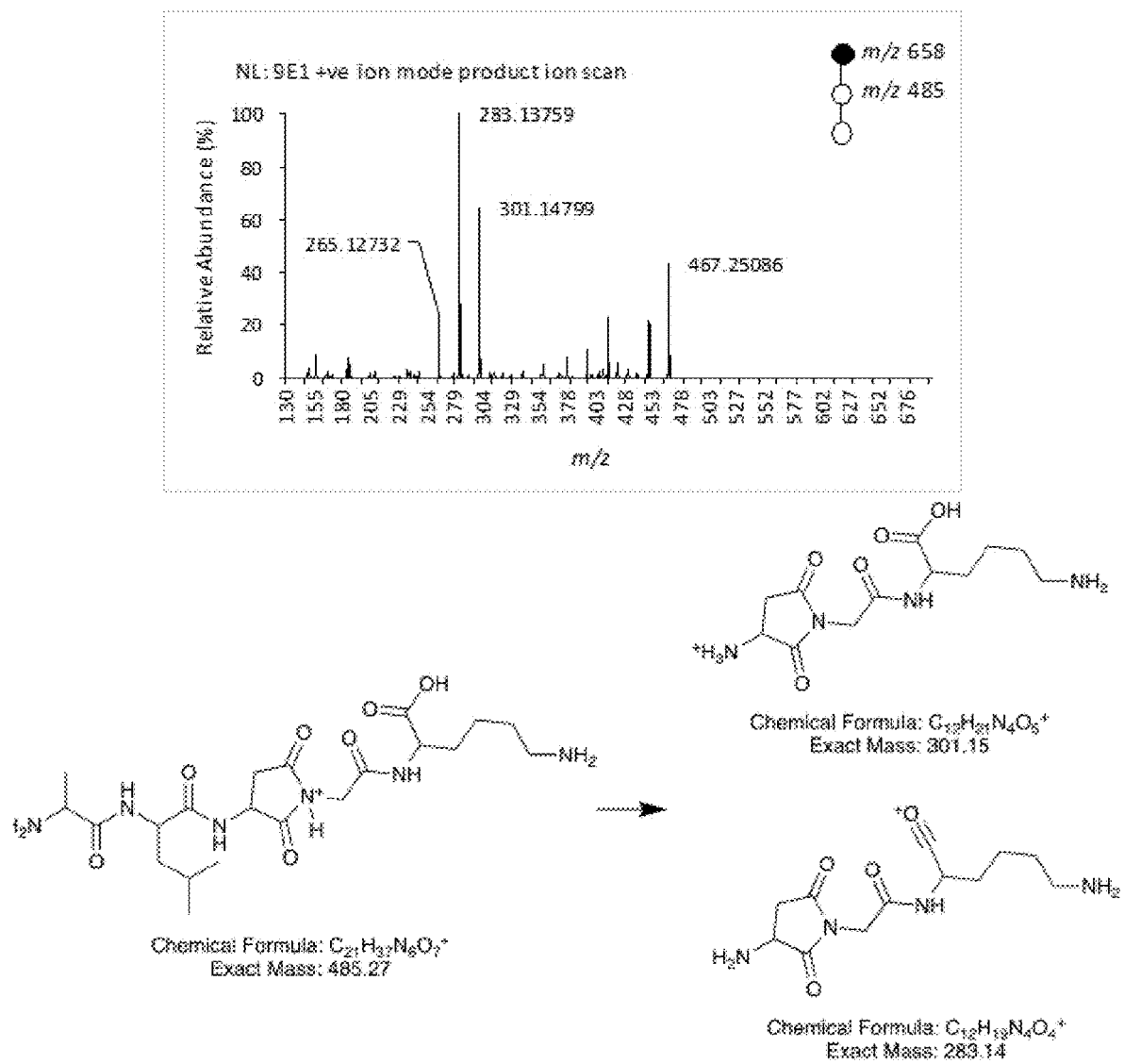
FIG. 5 shows the $MS^3$ product ion mass spectrum of ALDGK peptide bound to EDC and the structures corresponding to those ions.

Example 2: Analysis of $MS^n$ Mass Spectra of EDC-Bound Peptide to Confirm Succinimide Structure The spectrum in FIG. 5, generated using ALDGK peptide bound to EDC, showed that succimnimide formation is a route to the formation of the ion at m/z 485 in the $MS^2$ mass spectrum.

Figure 6A:
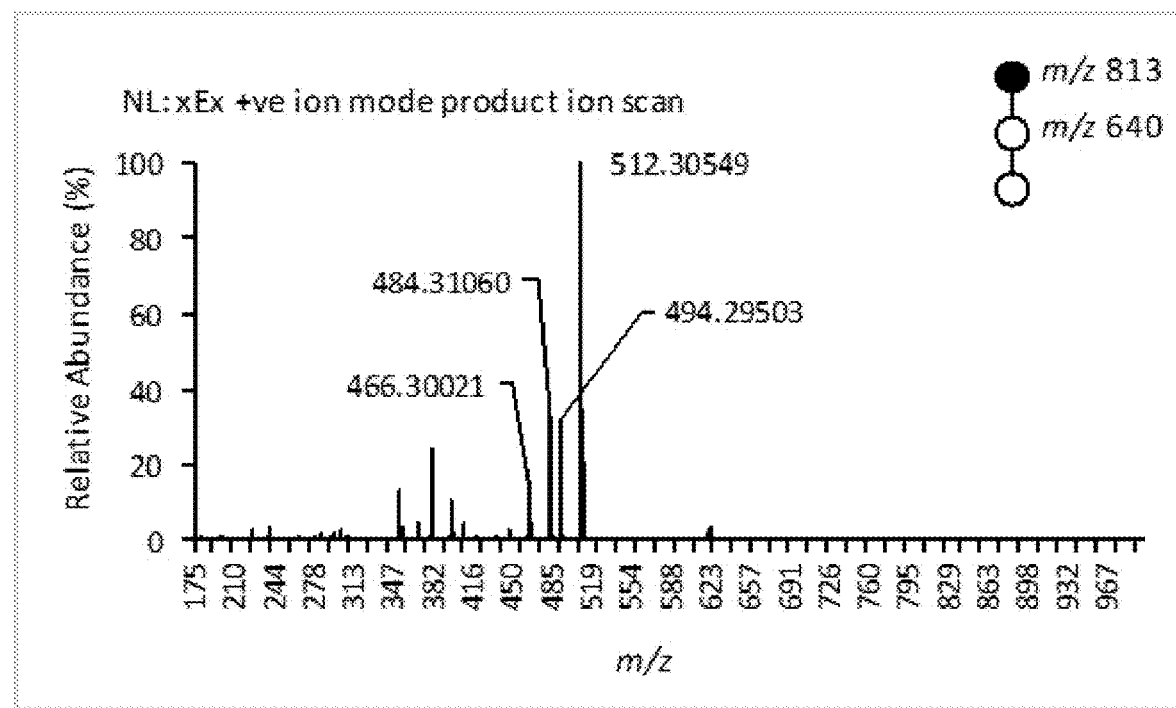
FIG. 6A and FIG. 6B show the $MS^3$ product ion mass spectrum of GDLLLK peptide-EDC and the proposed structures of the ions which are represented by the signals in the spectrum.
Figure 6B:
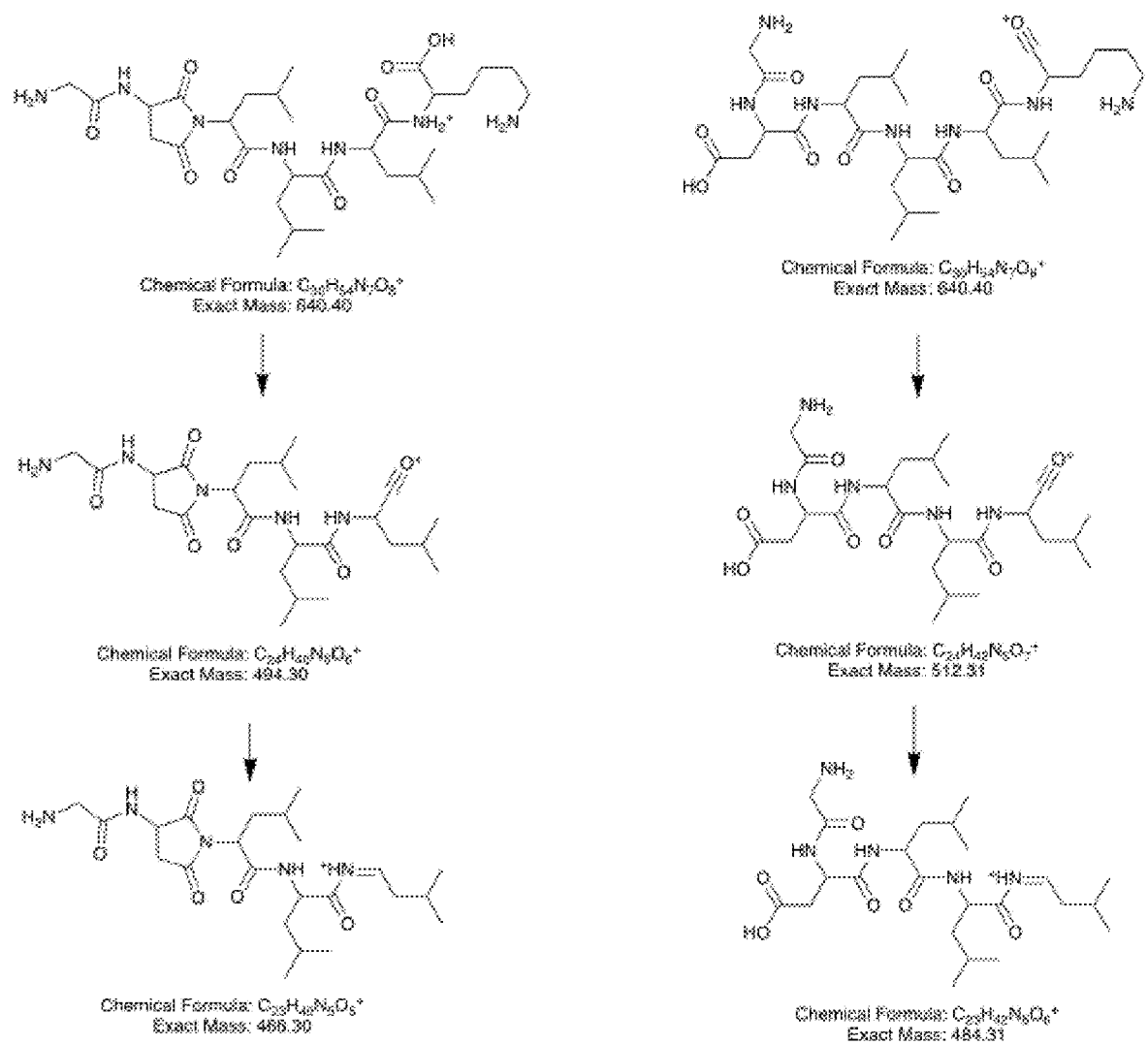

In the case of FIGS. 6A-B, there was observed a population of ions that fragmented from GDLLLK-EDC to which EDC was bound to the C-terminus. A second population of ions which results from the binding of EDC to the aspartate residue also was observed. These results suggest that the fragmentation of the latter population gives rise to the spectral differences in the $MS^2$ spectra.

Figure 7A:
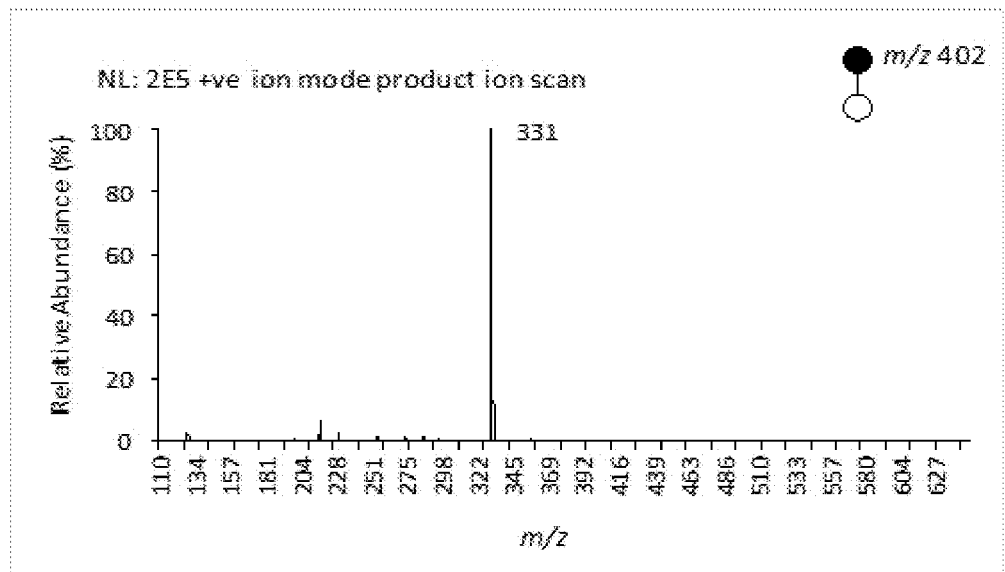
FIG. 7A and FIG. 7B show CID product ion mass spectrum of LD-EDC (FIG. 7A) and LDiso-EDC (FIG. 7B).
Figure 7B:
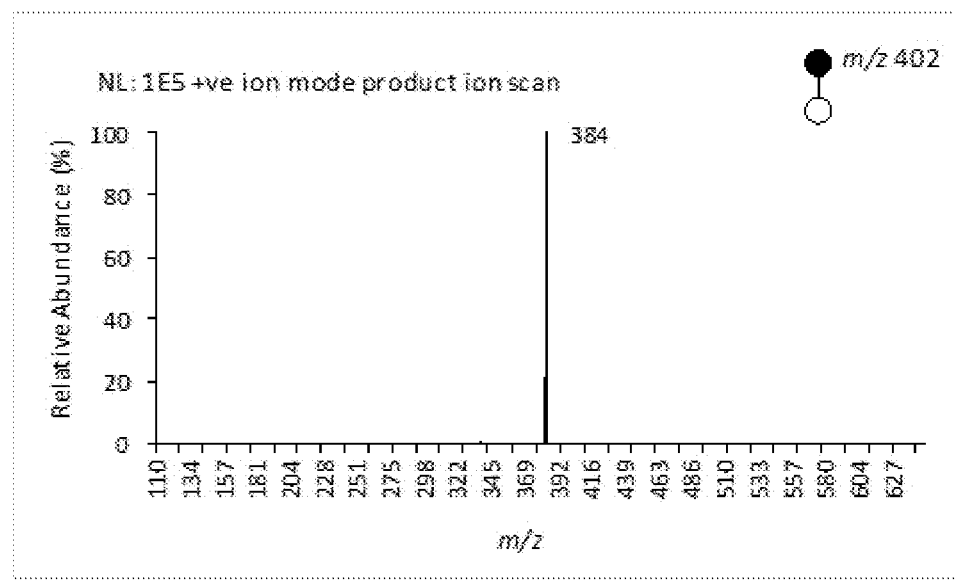

Example 3: LD(iso) Dipeptide, LD(iso)A Tripeptide, and GD(iso)LLLK Hexapeptide Spectra The fragmentation of LD dipeptide proceeded via distinctly orthogonal pathways (FIGS. 7A-B). In the case of aspartate, the loss of ethyl isocyanate dominated the spectrum, while in the case of isoaspartate, water loss dominated, which must logically come from the C-terminus. These results suggest that isocyanate was produced by the rearranged NAU and so these spectra show that the aspartate residue formed the NAU more favorably.

Figure 8A:
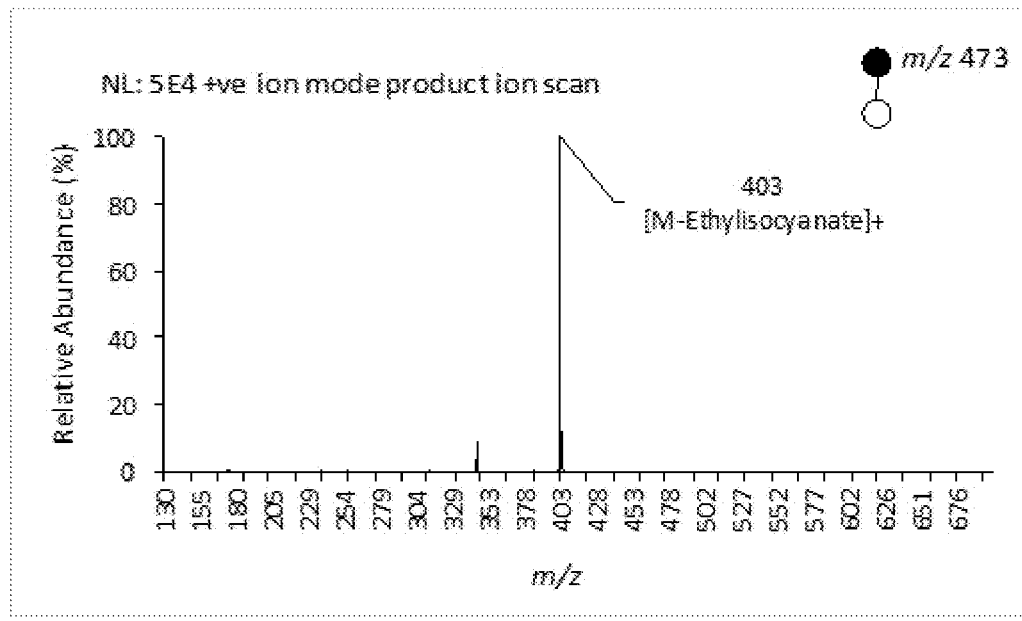
FIG. 8A and FIG. 8B show CID product ion mass spectrum of LDA (FIG. 8A) and LDisoA-EDC peptide (FIG. 8B).
Figure 8B:
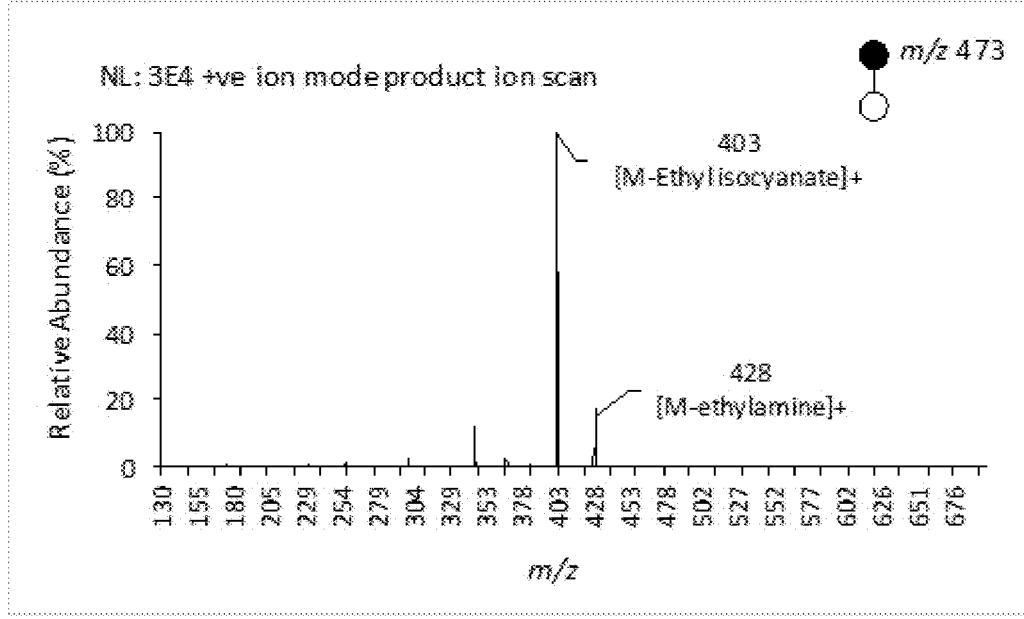

As shown in FIGS. 8A-B where LDA (FIG. 8A) and LDisoA-EDC tripeptides (FIG. 8B) were used to generate the spectra, there was observed a correlation to the spectra produced by LD. Since ethylamine could have only fragmented from the AiU isomer, while the NAU isomer could have almost exclusively fragmented to lose ethyl isocyanate with a secondary loss having been that of 3-dimethylaminopropyl isocyanate (m/z 345).

Figure 9A:
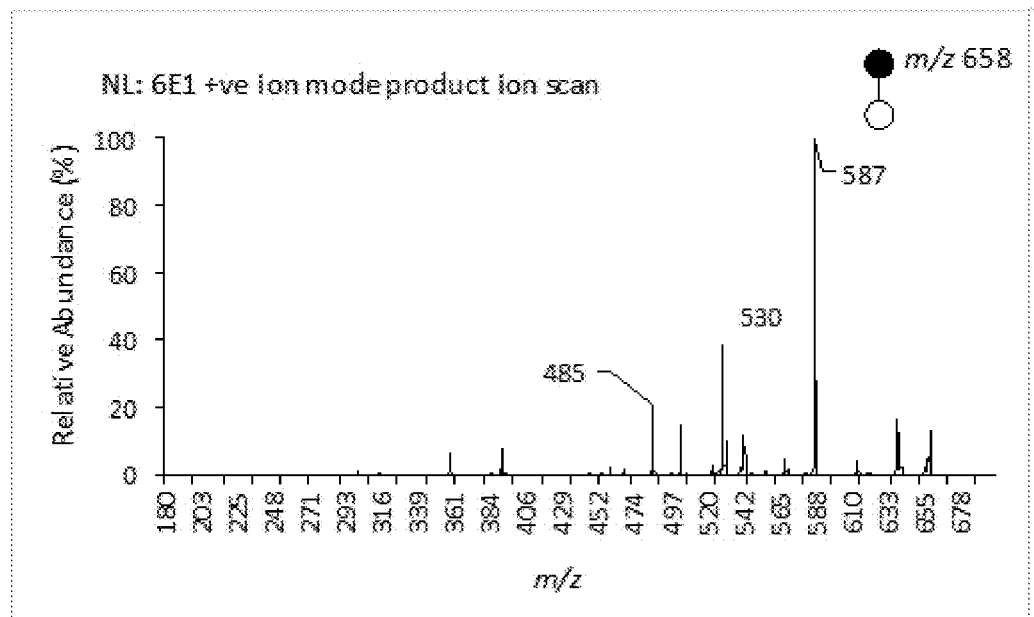
FIG. 9A and FIG. 9B show the CID product ion mass spectra of ALDGK peptide-EDC (FIG. 9A) and ALDisoGK peptide-EDC (FIG. 9B).
Figure 9B:
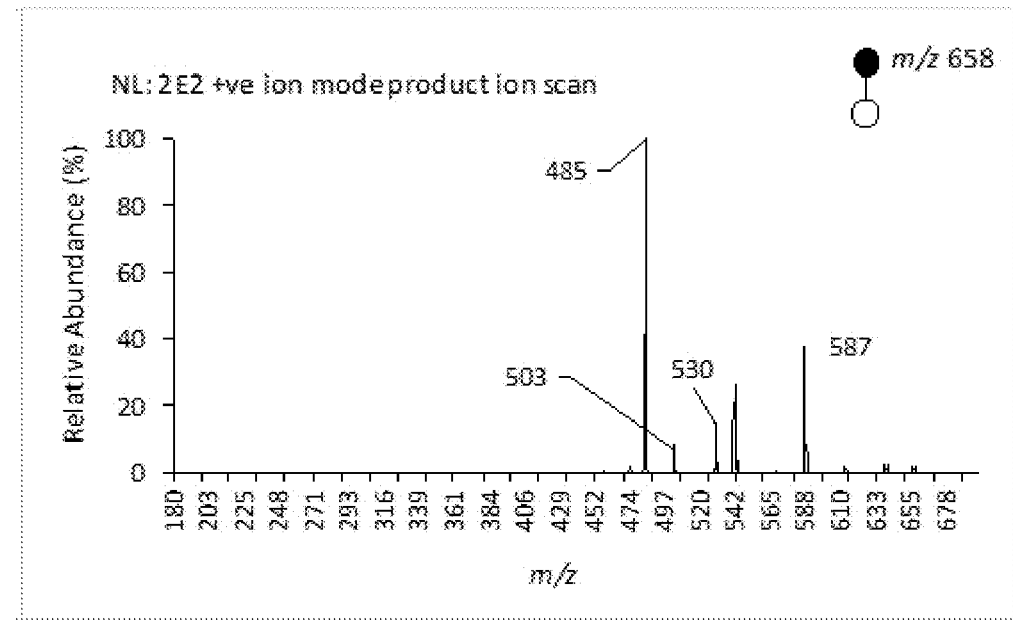

FIGS. 9A-B are mass spectra generated for ALDGK peptide-EDC (FIG. 9A) and ALDisoGK peptide-EDC (FIG. 9B) and showed a deviation in their fragmentation patterns from those of the shorter peptides shown in FIGS. 7 and 8; the ratio between the loss of EDU and the loss of ethyl isocyanate was now the one which provides good discrimination.

Figure 10A:
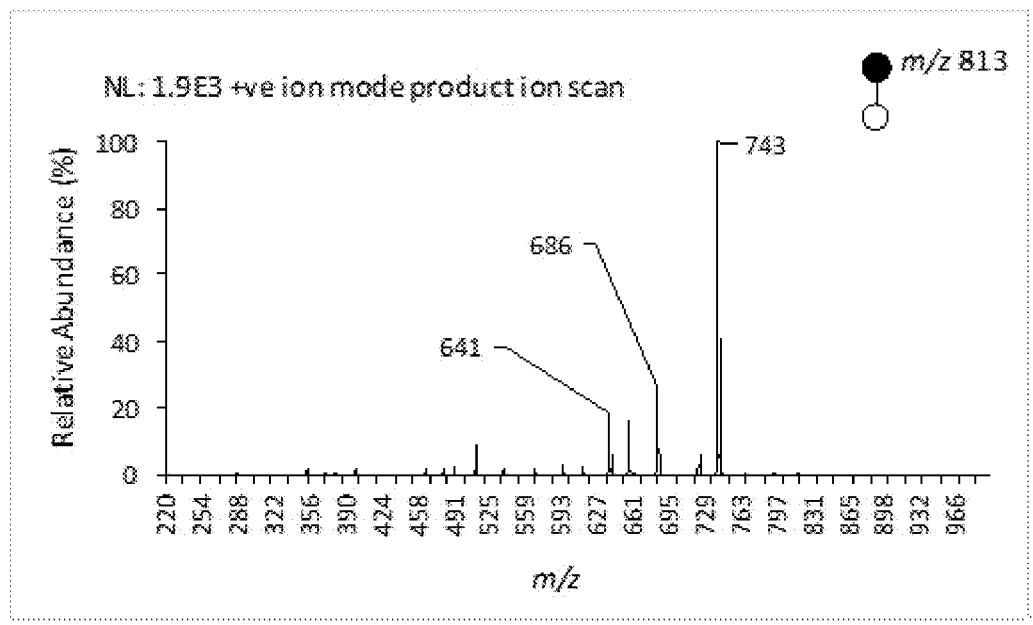
FIG. 10A and FIG. 10B show the CID product ion mass spectra of GDLLLK peptide-EDC (FIG. 10A) and GD(iso)LLLK peptide-EDC (FIG. 10B).
Figure 10B:
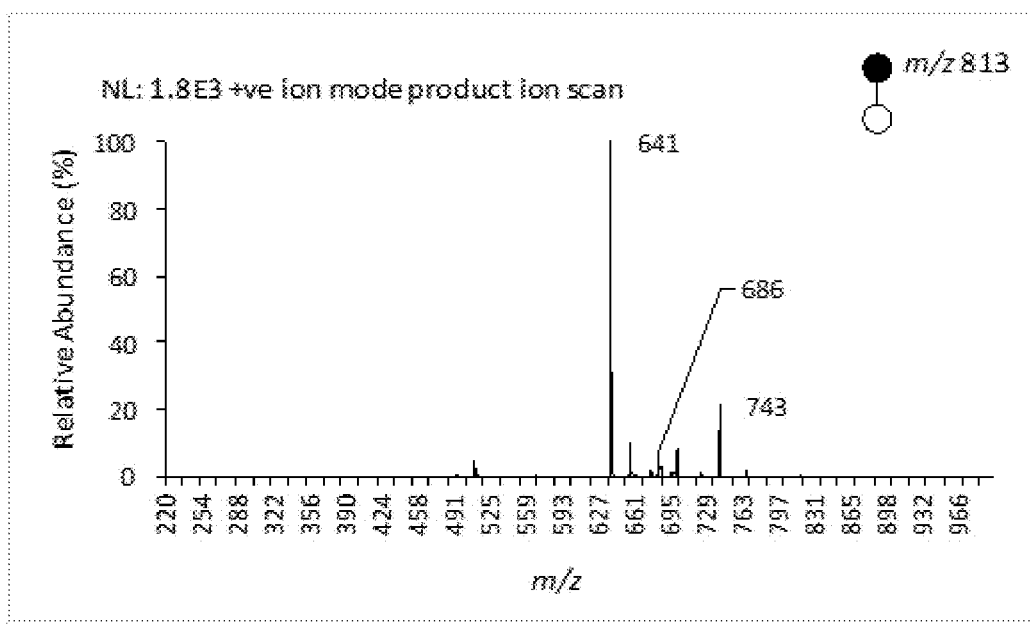

The mass spectra in FIGS. 10A-B illustrate that the hexapeptides GDLLLK-EDC (FIG. 10A) and GD(iso)LLLK-EDC (FIG. 10B) fragmented in an analogous fashion to the pentapeptides. There was observed a difference in the ion ratios, and these signals corresponded to the loss of isocyanates or the loss of EDU. The results showed the same trend as shown in FIGS. 8 and 9; fragmentation of aspartate-containing peptides favored the loss of isocyanates in their mass spectra, suggesting that they rearranged from the AiU to the NAU isomer more readily.

Example 4: Effects of Ion Activation Before Fragmentation and CID Energy

Figure 11A:
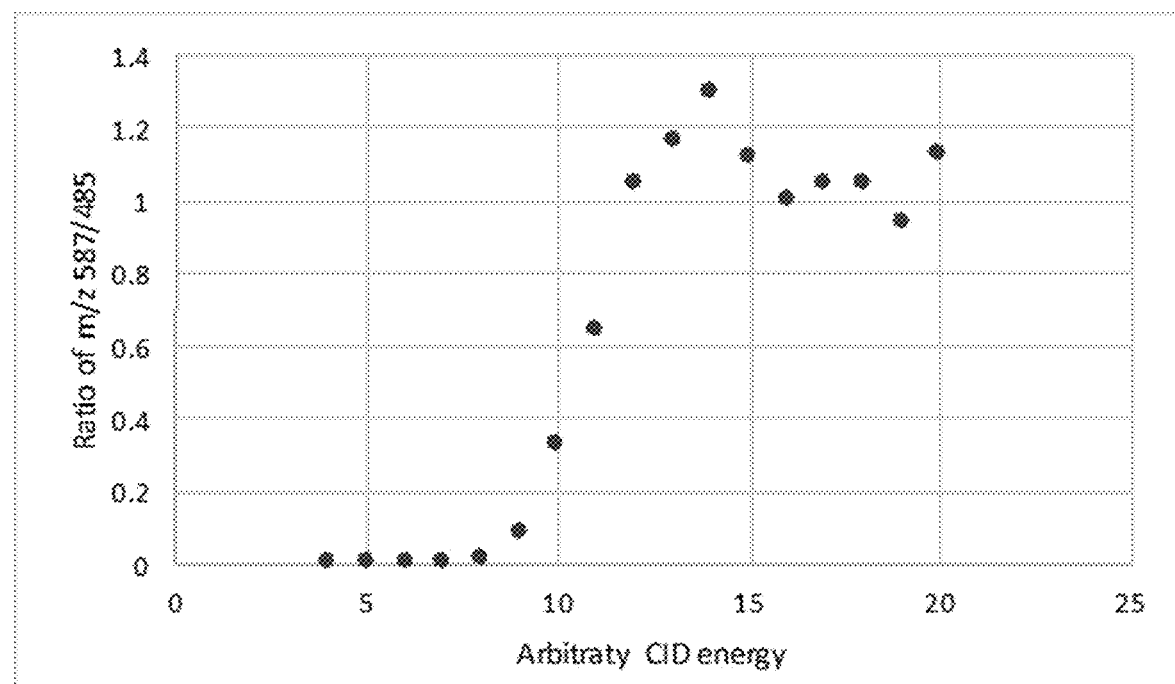
FIG. 11A, FIG. 11B, and FIG. 11C show effects of ion activation before fragmentation and CID energy.
Figure 11B:
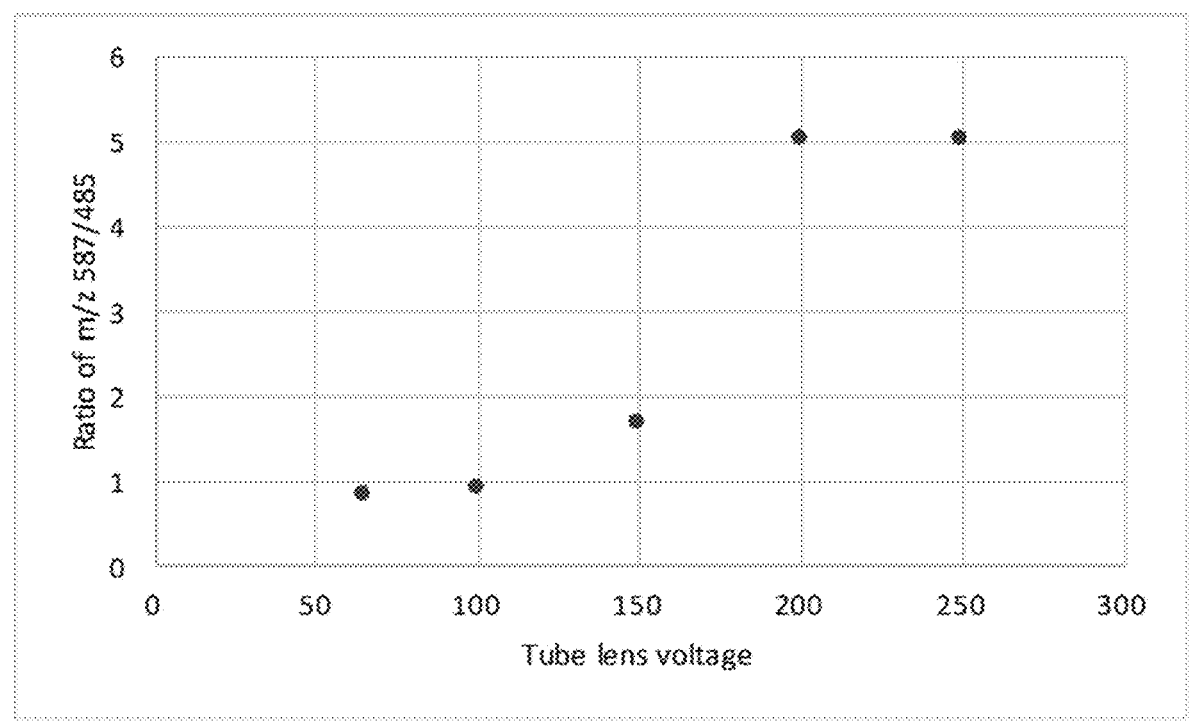
Figure 11C:
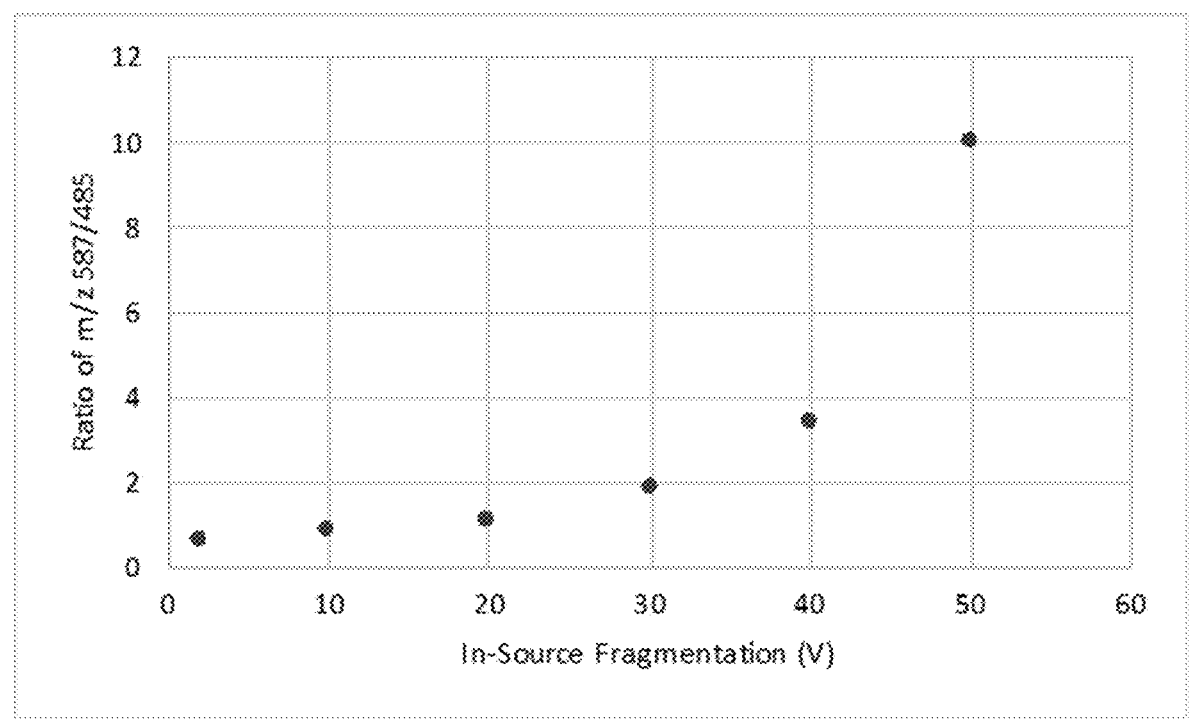

FIGS. 11A-C show effects of ion activation before fragmentation and CID energy. FIG. 11A shows the effect of ion activation energy on the ratios of the fragments of AiU/NAU in the CID product ion mass spectra of ALD(iso)GK. FIG. 11B shows the effect of the voltage applied to the tube lens on the ratios of the fragments of AiU/NAU in the CID product ion mass spectra of ALD(iso)GK. FIG. 11C shows the effect of in-source ion activation energy on the ratios of the fragments of iAU/NAU in the CID product ion mass spectra of ALD(iso)GK.

Example 5: CID Product Ion Mass Spectra of ALD(iso)GK and GD(iso)LLLK with Dicyclohexyl Carbodiimide (DCC) and Diispropylcarbodiimide (DIC)

Figure 12A:
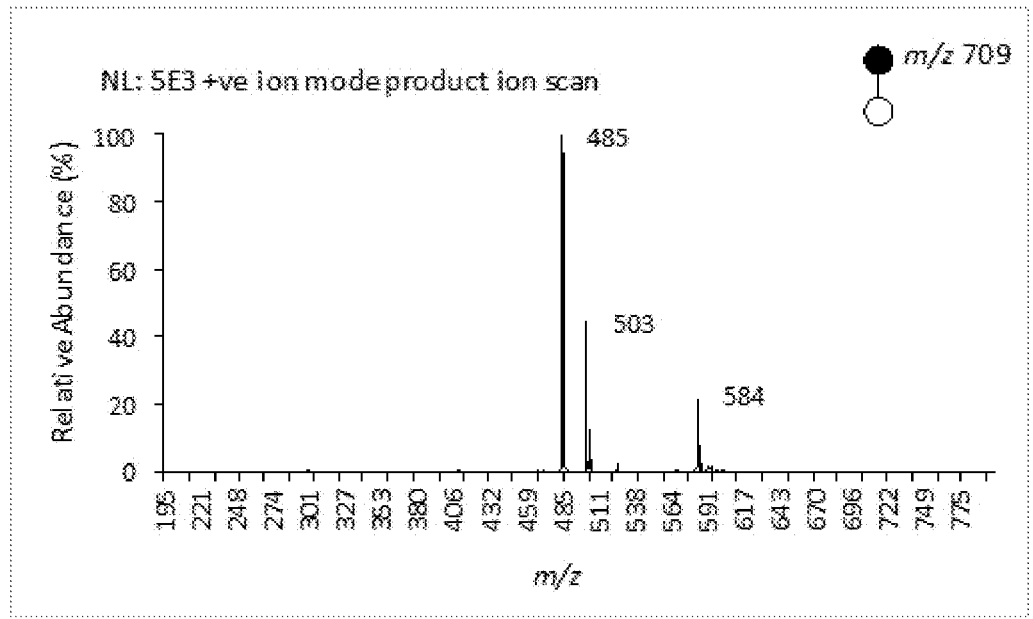
FIG. 12A and FIG. 12B show the CID product ion mass spectrum of protonated ALDGK peptide-DCC (FIG. 12A) and protonated ALDisoGK peptide-DCC (FIG. 12B).
Figure 12B:
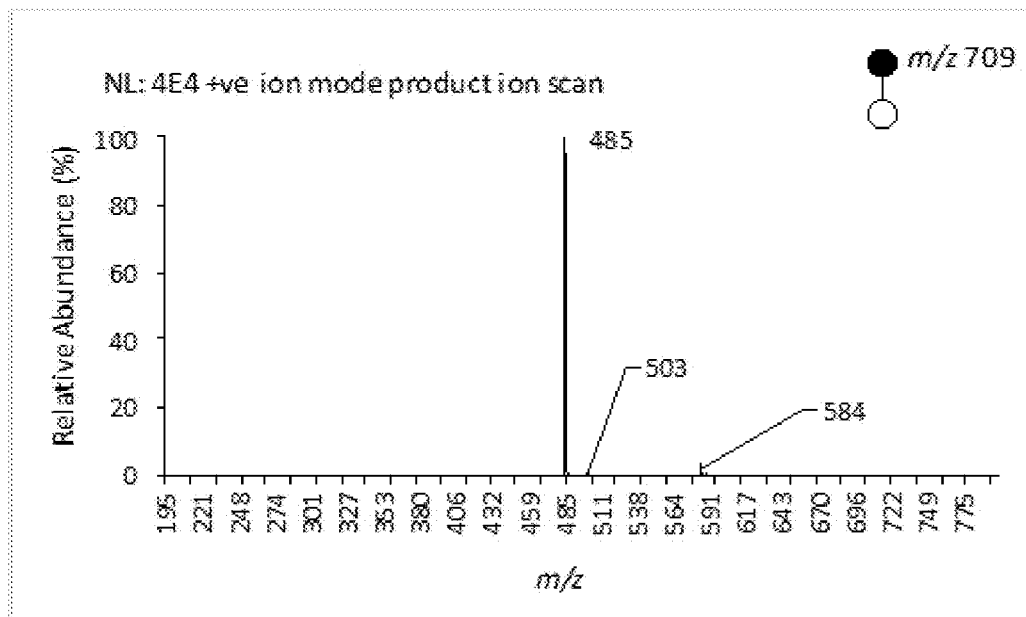

The spectra in FIGS. 12A-B (ALDGK peptide-DCC (FIG. 12A) and protonated ALDisoGK peptide-DCC (FIG. 12B)) showed the same trend as those spectra of peptides bound to EDC; the loss of the isocyanate (cyclohexylisocyanate) was favored in the spectrum of the aspartate-bearing peptide while the loss of the urea (in this case, dicyclohexylurea, DCU) was more dominant in the spectrum of the isoaspartate-bearing peptide. Notably, neither of the spectra showed a dominant signal corresponding to loss of the isocyanate, suggesting that rearrangement to the NAU was not favorable in either case. These results suggested that there is an extra quantity of steric hindrance imparted by the bulky cyclohexyl groups.

Figure 13A:
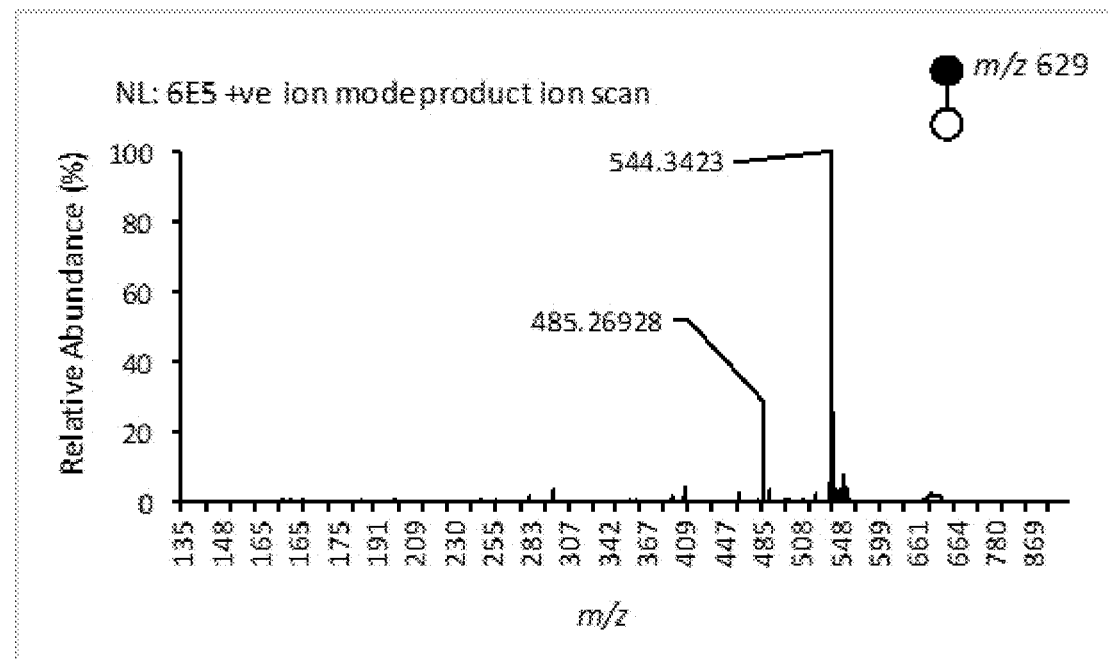
FIG. 13A and FIG. 13B show the CID product ion mass spectrum of protonated ALDGK peptide-DIC (FIG. 13A) and protonated ALDisoGK peptide-DIC (FIG. 13B).
Figure 13B:
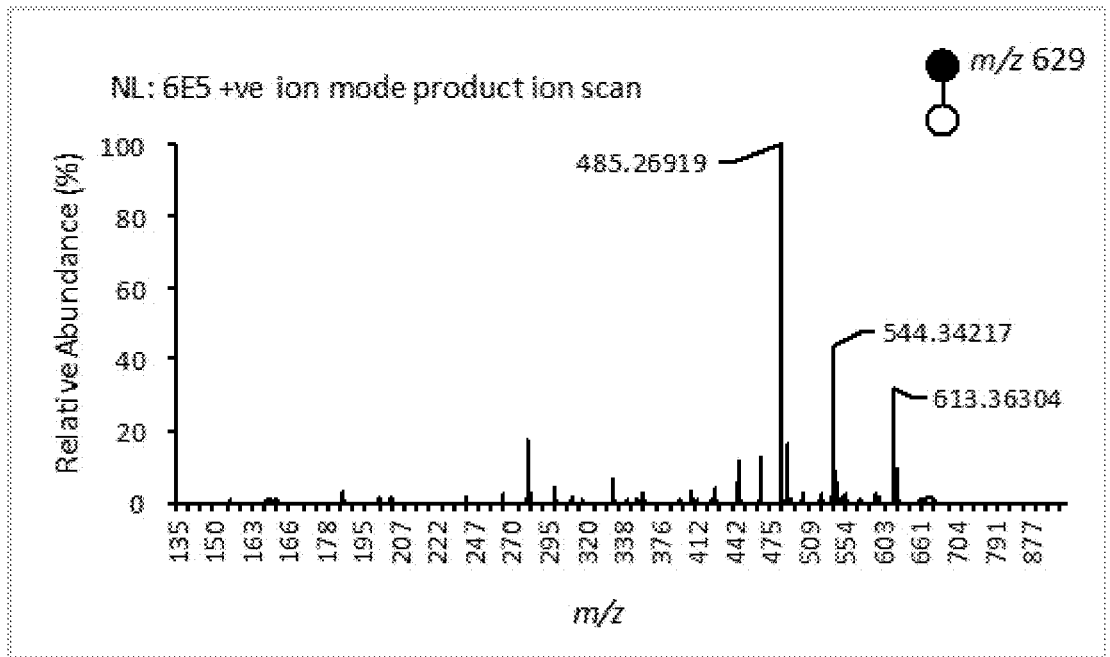

FIGS. 13A-B (ALDGK peptide-DIC (FIG. 13A) and protonated ALDisoGK peptide-DIC) showed the CID product ion mass spectra of protonated ALDGK/ALDisoGK bound to diisopropylcarbodiimide. This diimide is inherently less bulky than dicyclohexylcarbodiimide and this difference was reflected in the ratios of ions in the mass spectrum; in this case, the fragmentation of the rearranged NAU isomer was dominant in the spectrum of the aspartate-bearing peptide. Note that the total intensities were higher as these spectra were recorded on an orbitrap, which increases the signal level by about 2 orders of magnitude over the ion trap.

Figure 14A:
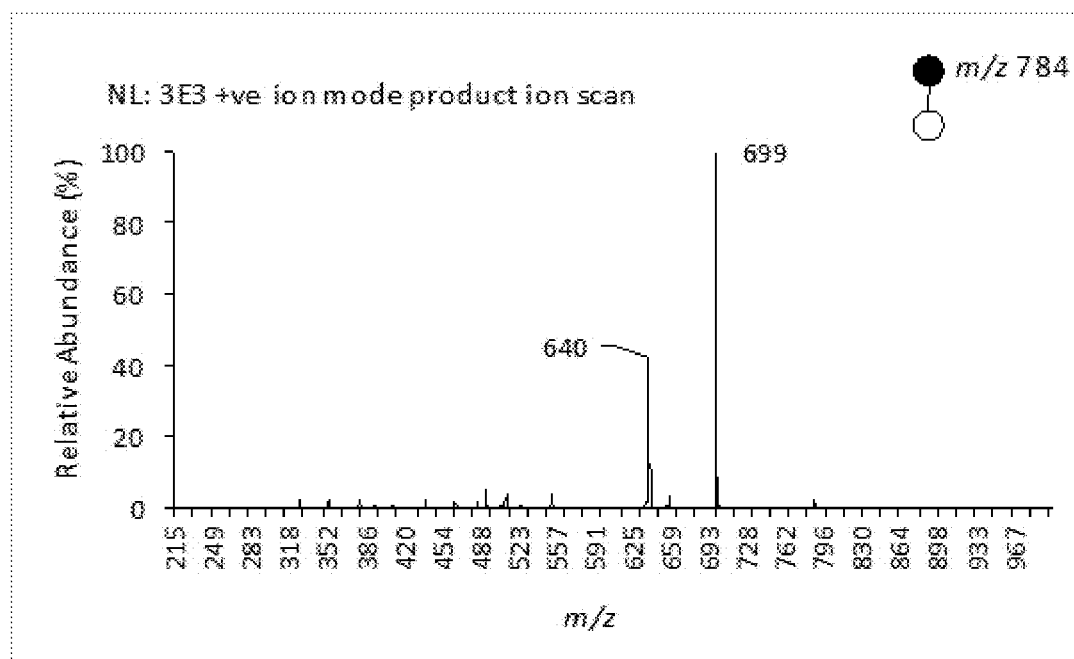
FIG. 14A and FIG. 14B show the CID product ion mass spectrum of protonated GDLLLK peptide-DIC (FIG. 14A) and protonated GDisoLLLK peptide-DIC (FIG. 14B).
Figure 14B:
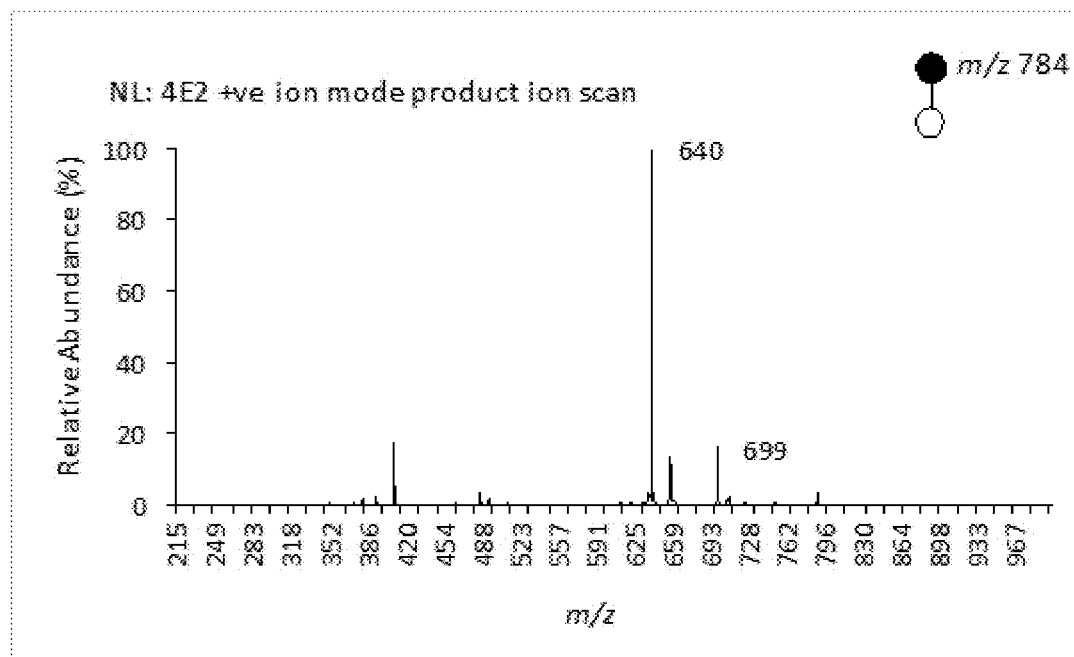

FIGS. 14A-B show the CID product ion mass spectra of the hexapeptides GDLLLK/GDisoLLLK bound to diisopropylcarbodiimide. Parallel to the results generated with this diimide for ALD(iso)GK, the spectrum of GDisoLLLK showed a dominant loss of isocyanate.

Example 6: Calibration Curves Generated from GD(iso)LLLK and LD(iso)A

Figure 15A:
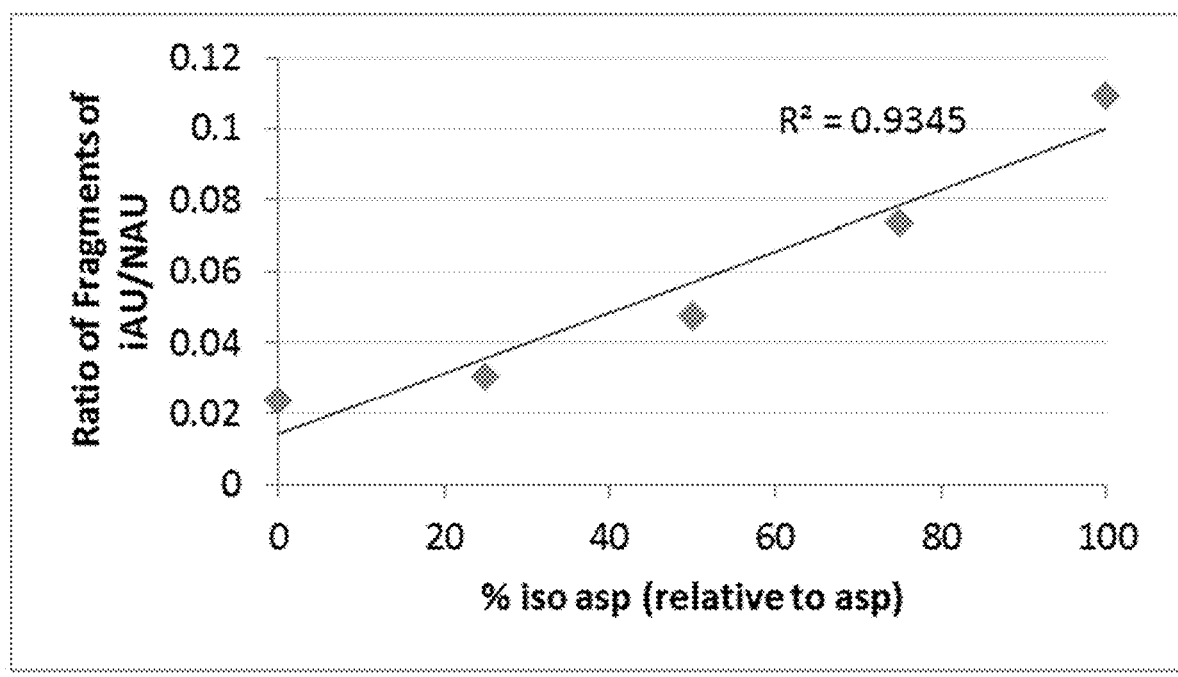
FIG. 15A is a calibration of the ratio of D/Diso in lD(iso)A.
Figure 15B:
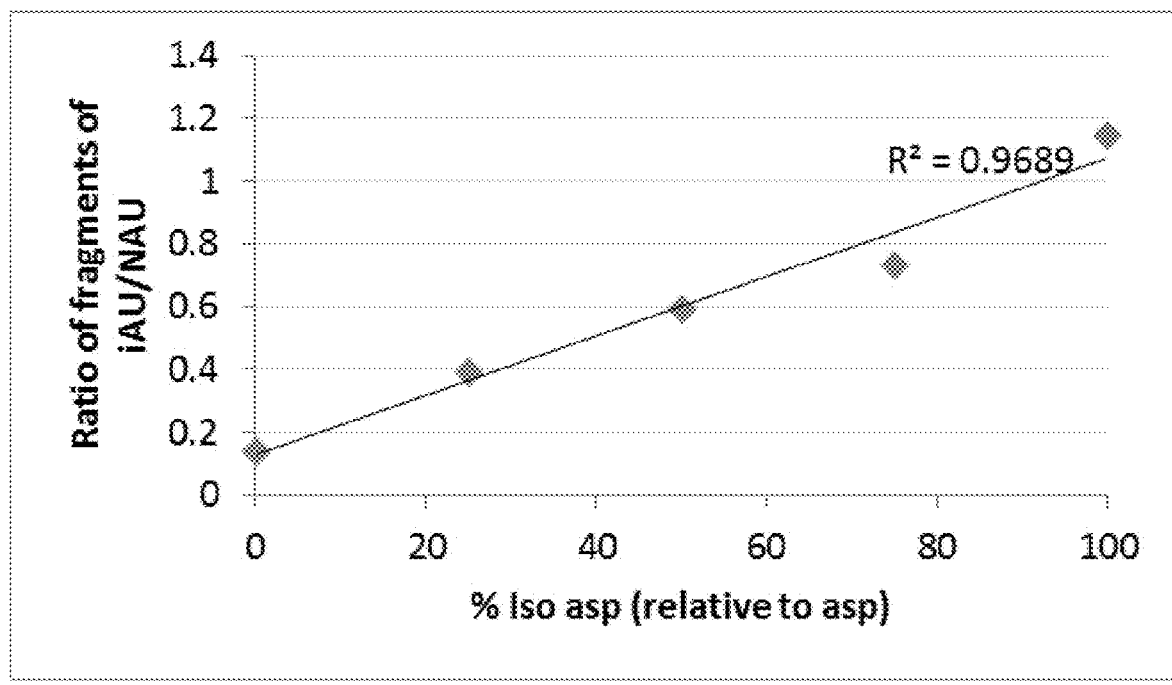
FIG. 15B is a Calibration of the ratio of D/Diso in GD(iso)LLLK.

FIGS. 15A-B are calibration curves for the trimeric peptide, ID(iso)A (FIG. 15A) and the hexameric peptide GD(iso)LLLK (FIG. 15B). Although the fragmentation pathways which discriminate between D/Diso in each case were different, calibration can be achieved with similar results in both cases.

REFERENCES

1. Kozin, S. A.; Mitkevich, V. A.; Makarov, A. A., Amyloid-beta containing isoaspartate 7 as potential biomarker and drug target in Alzheimer's disease. Mendeleev Commun. 2016, 26, 269-275.
2. Shimizy, T.; Matsuoka, Y.; Shirasawa, T., Biological Significance of Isoaspartate and Its Repair System. Biol. Pharm. Bull. 2005, 28 (9), 1590-1596.
3. Liu, M.; Cheetham, J.; Cauchon, N.; Ostovic, J.; Ni, W.; Ren, D.; Zhou, Z. S., Protein isoaspartate methyltransferase-mediated 18O-labeling of isoaspartic acid for mass spectrometry analysis. Anal. Chem. 2012, 84 (2), 1056-62.
4. Puri, A.; Quan, Y.; Narang, A. S.; Adams, M.; Gandhi, R.; Nashine, V. C., A Fluorescence-Based High-Throughput Coupled Enzymatic Assay for Quantitation of Isoaspartate in Proteins and Peptides. AAPS PharmSciTech 2017, 18 (3), 803-808.
5. Winter, D.; Pipkorn, R.; Lehmann, W. D., Separation of peptide isomers and conformers by ultra performance liquid chromatography. J. Sep. Sci. 2009, 32 (8), 1111-9.
6. Ni, W.; Di, S.; Karger, B. L.; Zhou, Z. S., Analysis of Isoaspartic Acid by Selective Proteolysis with Asp-N and Electron Transfer Dissociation Mass Spectrometry. Anal. Chem. 2010, 82, 7485-7491.
7. Yu, X.; Sargaeva, N. P.; Thompson, C. J.; Costello, C. E.; Lin, C., In-Source Decay Characterization of Isoaspartate and beta-Peptides. Int. J. Mass spectrom. 2015, 390, 101-109.
8. McLafferty, F. W., Molecular Rearrangements. Anal. Chem. 1959, 31 (1), 82-87.
9. Bowen, R. D., Ion-Neutral Complexes. Acc. Chem. Res. 1991, 24 (12), 364-371.
10. Carpino, L. A.; El-Faham, A., The Diisopropylcarbodiimide/1-Hydroxy-7-Azabenzotriazole System: Segment Coupling and Stepwise Peptide Assembly Tetrahedron 1999, 55, 6813-6830.
11. DeTar, D. F.; Silverstein, R., Reactions of Carbodiimides. I. The Mechanisms of the Reactions of Acetic Acid with Dicyclohexylcarbodiimide J. Am. Ceram. Soc. 1966, 85 (5), 1013-1019.
12. DeTar, D. F.; Silverstein, R., Reactions of Carbodiimides. II. Thre Recactiosn of Dicyclohexylcarbodiimide with Carboxylic Acids in the Presence of Amines and Phenols. J. Am. Ceram. Soc. 1966, 88 (5), 1020-1023.
13. DeTar, D. F.; Silverstein, R.; F., R. J. F., Reactions of Carbodiimides. III. The Reactions of Carbodiimides with Peptide Acids J. Am. Chem. Soc. 1966, 88 (5), 1024-1030.
14. G., K. H., The Chemistry of Carbodiimides. Chem. Rev. 1953, 53 (2), 145-166.
15. Giles, M. A.; Hudson, A. Q.; Borders Jr., C. L., Stability of Water-Soluble Carbodiimides in Aqueous Solution Anal. Biochem. 1990, 184, 244-248.
16. Iwasawa, T.; Wash, P.; Gibson, C.; Rebek Jr., J., Reaction of Introverted Carboxylic Acid with Carbodiimide. Tetrahedron 2007, 63 (28), 6505-6511.
17. Kurzer, F.; Douraghi-Zadeh, K., Advances in the Chemistry of Carbodiimides Chem. Rev. 1967, 62 (2), 107-152.
18. Nakajima, N.; Ikada, Y., Mechanism of Amide Formation by Carbodiimide for Bioconjugation in Aqueous Media. Bioconjugate Chem. 1955, 6, 123-130.
19. Schotman, A. H. M., Mechanism of reaction of carbodiimides with carboxylic acids. Recl. Tray. Chim. Pays-Bas 1991, 110, 319-324.

What is claimed is:

1. A method for determining whether a peptide comprises aspartate or isoaspartate, the method comprising:
    binding an aspartate/isoaspartate residue in a peptide with a label, to produce a labeled peptide; ionizing the labeled peptide, wherein the ionizing causes the label to undergo rearrangement in a gas phase at a higher rate if the label is bound to an aspartate residue as compared to if the label is bound to an isoaspartate residue, wherein the label is a compound that comprises a carbodiimide group; and
    performing a mass spectrometry analysis to detect the rearrangement of the label, thereby determining whether the peptide comprises aspartate or isoaspartate.

2. The method according to claim 1, wherein the label is 1-ethyl-3-(3-dimethylaminopropyl)carbodiimide (EDC) or dicyclohexyl carbodiimide (DCC).

3. The method according to claim 2, wherein the EDC binds a carboxylate group of the aspartate/isoaspartate residue.

4. The method according to claim 3, wherein the rearrangement comprises production of N-acylurea (NAU).

5. The method according to claim 4, wherein the mass spectrometry analysis to detect the rearrangement of the label comprises collision induced dissociation of the NAU to detect ethyl isocyanate ions.

6. The method according to claim 5, wherein the mass spectrometry analysis also detects the labeled peptide as acylisourea (AiU).

7. The method according to claim 6, wherein the mass spectrometry analysis to detect the AiU comprises collision induced dissociation of the AiU to detect fragment ions of the AiU.

8. The method according to claim 7, further comprising quantifying an amount of isoaspartate in the peptide by determining a ratio of the ethyl isocyanate ions to the fragment ions of the AiU.

9. The method according to claim 1, further comprising providing a sample comprising a protein that comprises the aspartate/isoaspartate residue and digesting the protein to produce the peptide that comprises the aspartate/isoaspartate residue.

10. A method for determining whether a peptide comprises aspartate or isoaspartate, the method comprising: detecting a gas phase rearrangement of a label bound to an aspartate/isoaspartate residue of a peptide, wherein the label rearranges at a higher rate in the gas phase if the label is bound to the aspartate residue as compared to if the label is bound to the isoaspartate residue, and wherein the label is a compound that comprises a carbodiimide group.

11. The method according to claim 10, wherein the label is 1-ethyl-3-(3-dimethylaminopropyl)carbodiimide (EDC) or dicyclohexyl carbodiimide (DCC).

12. The method according to claim 11, wherein the EDC binds a carboxylate group of the aspartate/isoaspartate residue.

13. The method according to claim 12, wherein the rearrangement comprises production of N-acylurea (NAU).

14. The method according to claim 13, wherein detecting comprises performing a mass spectrometry analysis to detect the rearrangement of the label by collision induced dissociation of the NAU to detect ethyl isocyanate ions.

15. The method according to claim 14, wherein the method further comprises detecting the labeled peptide as acylisourea (AiU).

16. The method according to claim 15, wherein detecting comprising performing a mass spectrometry analysis to detect the AiU by collision induced dissociation of the AiU to detect fragment ions of the AiU.

17. The method according to claim 16, further comprising quantifying an amount of isoaspartate in the peptide by determining a ratio of the ethyl isocyanate ions to the fragment ions of the AiU.

18. The method according to claim 10, further comprising providing a sample comprising a protein that comprises the aspartate/isoaspartate residue and digesting the protein to produce the peptide that comprises the residue.

* * * * *